United States Patent [19]

Matsuo et al.

[11] Patent Number: 5,034,417

[45] Date of Patent: Jul. 23, 1991

[54] NEW ALKANESULFONANILIDE DERIVATIVES, PROCESSES FOR PREPARATION THEREOF AND PHARMACEUTICAL COMPOSITION COMPRISING THE SAME

[75] Inventors: Masaaki Matsuo, Toyonaka; Kiyoshi Tsuji, Kishiwada; Nobukiyo Konishi, Nagaokakyo; Hiroyuki Okumura, Ibaraki, all of Japan

[73] Assignee: Fujisawa Pharmaceutical Co., Ltd., Osaka, Japan

[21] Appl. No.: 197,966

[22] Filed: May 24, 1988

[30] Foreign Application Priority Data

May 29, 1987 [GB] United Kingdom ............... 8712647
Oct. 23, 1987 [GB] United Kingdom ............... 8724903
Jan. 15, 1988 [GB] United Kingdom ............... 8800871

[51] Int. Cl.$^5$ ............... A61K 31/18; C07C 323/67; C07C 311/45; C07C 311/33
[52] U.S. Cl. ............... 514/605; 564/97; 564/99; 564/36; 558/413; 562/430; 548/197; 548/186; 548/329; 548/251; 544/281; 547/294; 547/157; 549/65
[58] Field of Search ............... 564/97, 99; 514/605

[56] References Cited

U.S. PATENT DOCUMENTS

| Re. 29,032 | 11/1976 | Robertson | 564/97 |
|---|---|---|---|
| 3,178,339 | 4/1965 | Frick et al. | 514/605 |
| 3,223,582 | 12/1965 | Bindler et al. | 564/99 X |
| 3,755,605 | 8/1973 | Moore et al. | 514/605 |
| 3,840,597 | 10/1974 | Moore et al. | 564/97 |
| 3,856,859 | 12/1974 | Moore et al. | 564/99 |
| 3,972,926 | 8/1976 | Moore et al. | 564/97 |
| 4,321,081 | 3/1982 | Konishi et al. | 564/97 X |
| 4,349,378 | 9/1982 | Cliff et al. | 514/605 X |
| 4,675,405 | 6/1987 | Musser et al. | 546/172 |
| 4,738,711 | 4/1988 | Barton et al. | 562/474 X |
| 4,780,128 | 10/1988 | Cartwright | 564/99 X |
| 4,866,091 | 9/1989 | Matsuo et al. | 514/424 X |

FOREIGN PATENT DOCUMENTS

| 149423 | 7/1985 | European Pat. Off. | 564/97 |
|---|---|---|---|
| 273369 | 7/1988 | European Pat. Off. | 564/97 |
| 2845996 | 4/1980 | Fed. Rep. of Germany | 564/97 |
| 48-27298 | 8/1973 | Japan . | |
| 49-42640 | 4/1974 | Japan . | |
| 55-57507 | 4/1980 | Japan . | |
| 55-57556 | 4/1980 | Japan . | |
| 55-124753 | 9/1980 | Japan . | |
| 56-16461 | 2/1981 | Japan . | |
| 57-136560 | 8/1982 | Japan . | |
| 57-140712 | 8/1982 | Japan . | |
| 57-175154 | 10/1982 | Japan . | |
| 57-200340 | 12/1982 | Japan . | |
| 58-35989 | 8/1983 | Japan . | |
| 58-50984 | 11/1983 | Japan . | |
| 59-16871 | 1/1984 | Japan | 564/97 |
| 59-31755 | 2/1984 | Japan . | |
| 59-44311 | 10/1984 | Japan . | |
| 61-10548 | 1/1986 | Japan . | |

OTHER PUBLICATIONS

Journal of Medical Chemistry, 1975, vol. 18, No. 4, pp. 386–391, Moore et al, "Antiinflammatory Fluoroalkanesulfonanilides, . . . ".

*Primary Examiner*—Carolyn Elmore

[57] ABSTRACT

This invention relates to new alkanesulfonanilide derivatives and pharmaceutically acceptable salts thereof which have inflammatory activities and analgesic activities, to pharmaceutical compositions containing the same and to a method for the treatment of inflammatory disease or pains in human beings and animals.

14 Claims, No Drawings

NEW ALKANESULFONANILIDE DERIVATIVES, PROCESSES FOR PREPARATION THEREOF AND PHARMACEUTICAL COMPOSITION COMPRISING THE SAME

This invention relates to new alkanesulfonanilide derivatives and pharmaceutically acceptable salts thereof. More particularly, it relates to alkanesulfonanilide derivatives and pharmaceutically acceptable salts thereof which have antiinflammatory activities and analgesic activities, to processes for the preparation thereof, to a pharmaceutical composition comprising the same and to a method for the treatment of inflammatory disease or pains in human being and animals.

The objective alkanesulfonanilide derivatives and pharmaceutically acceptable salts thereof are novel and can be represented by the following general formula (I):

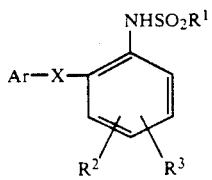

wherein
Ar is a group of the formula:

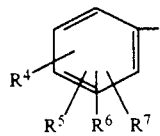

wherein $R^4$, $R^5$, $R^6$ and $R^7$ are each hydrogen, halogen, halo(lower)alkyl or lower alkoxy, or heterocyclic group which may have halogen or lower alkyl,
X is

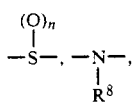

—CO—, —NHCO—, —COHN— or

wherein n is 0, 1 or 2, $R^8$ is hydrogen or lower alkyl, $R^9$ is hydrogen or hydroxy,
$R^1$ is lower alkyl or halo(lower)alkyl,
$R^2$ is acyl, cyano, carboxy, lower alkyl which may have one or more substituents selected from hydroxy, amino and benzyl, lower alkylthio, lower alkylsulfonyl, lower alkanoyl(lower)alkenyl, heterocyclic group which may have amino or lower alkylsulfonylamino, or a group of the formula:

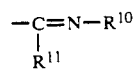

wherein
$R^{10}$ is hydroxy, ureido or lower alkoxy,
$R^{11}$ is lower alkyl, and
$R^3$ is hydrogen, nitro, lower alkyl or halogen, and pharmaceutically acceptable salts thereof.

According to this invention, the new alkanesulfonanilide derivatives (I) and salts thereof can be prepared by various processes which are illustrated by the following reaction schemes:

Process 1

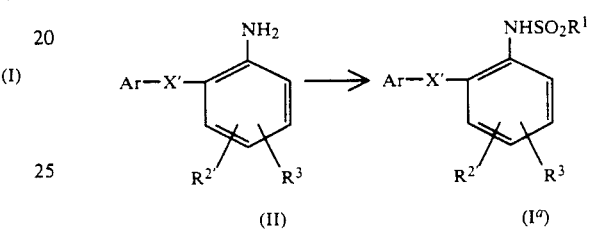

Process 2

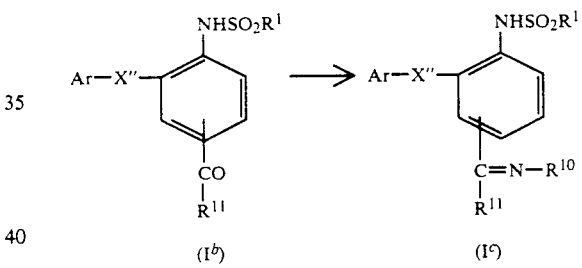

Process 3

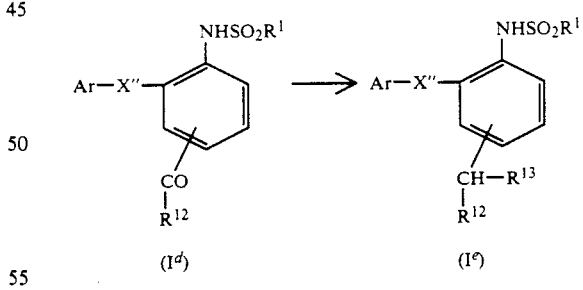

Process 4

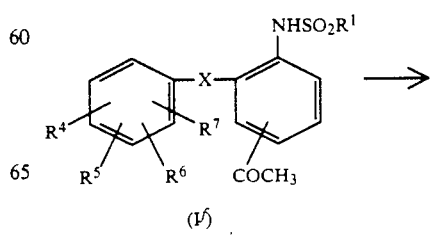

5,034,417
-continued
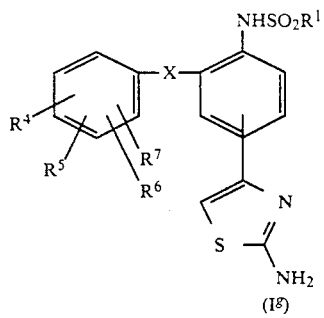
(Iᵍ)
Process 5
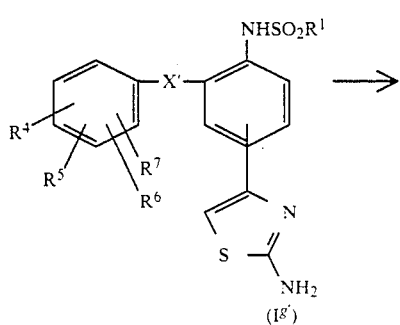
(Iᵍ')
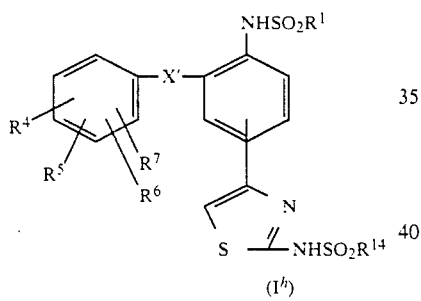
(Iʰ)
Process 6
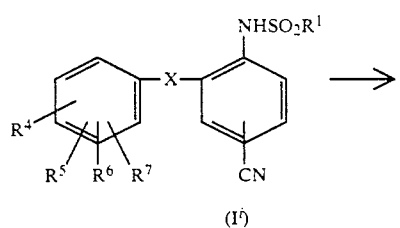
(Iᶠ)
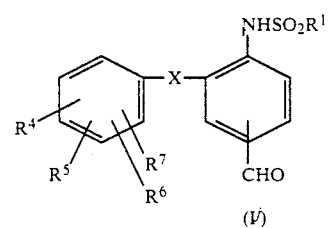
(V)
Process 7
-continued
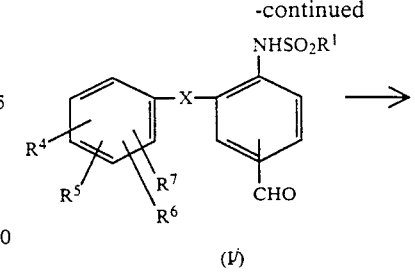
(V)
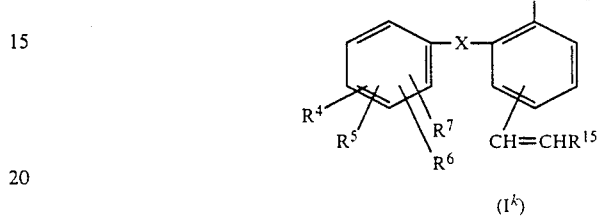
(Iᵏ)
Process 8
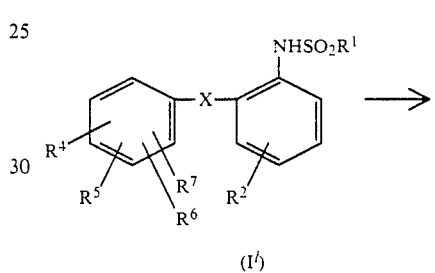
(Iˡ)
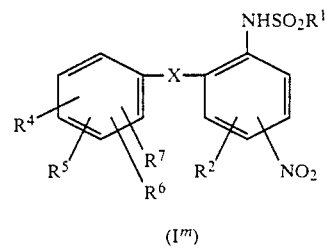
(Iᵐ)
Process 9
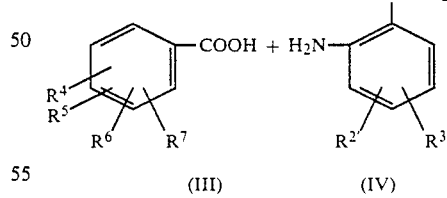
(III)   (IV)
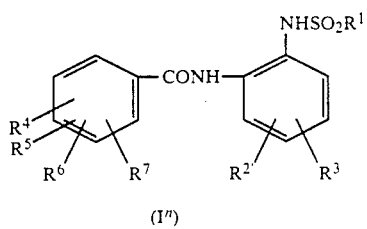
(Iⁿ)
Process 10

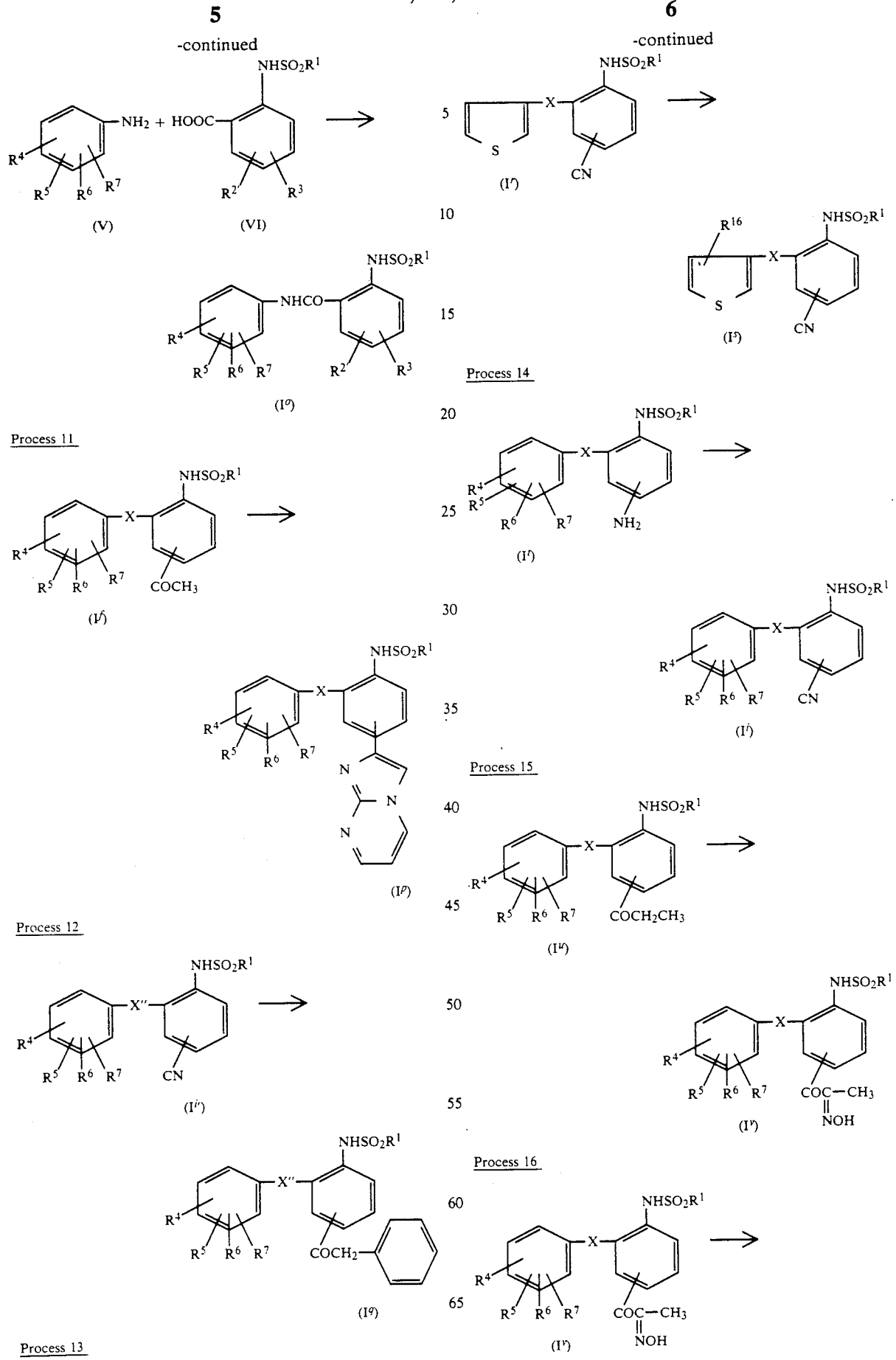

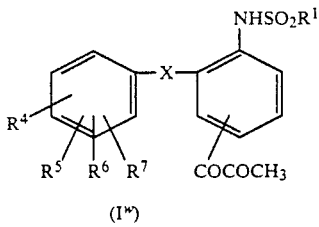

(I'")

Process 17

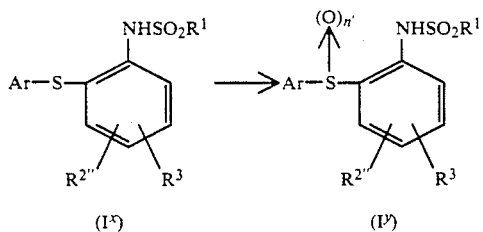

In the above formulae, X' is the same as defined in X excepting

X" is the same as defined in X excepting —CO—, $R^{12}$ is hydrogen, lower alkyl or benzyl, $R^{13}$ is hydroxy or amino, $R^{14}$ is lower alkyl, $R^{15}$ is lower alkanoyl, $R^{16}$ is halogen, $R^{2'}$ is the same as defined in $R^2$ excepting lower alkyl which have hydroxy or amino, heterocyclic group which have amino, and a group of the formula:

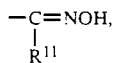

$R^{2''}$ is the same as defined in $R^2$ excepting lower alkylthio, n' is 1 or 2, and Ar, X, and $R^1$ to $R^7$ are each as defined before.

Preferred pharmaceutically acceptable salts of the object compound (I) are conventional non-toxic salts and may include a salt with a base such as a salt with an inorganic base, for example, an alkali metal salt (e.g. lithium salt, sodium salt, potassium salt, etc.), an alkaline earth metal salt (e.g. calcium salt, magnesium salt, etc.), an ammonium salt; a salt with an organic base, for example, an organic amine salt (e.g. triethylamine salt, ethanolamine salt, triethanolamine salt, dicyclohexylamine salt, N,N'-dibenzylethylenediamine salt, etc.), an inorganic acid salt (e.g. hydrochloride, hydrobromide, sulfate, etc.) and an organic acid salt (e.g. formate, acetate, 2,2,2-trifluoroacetate, p-toluenesulfonate, etc.) and the like.

Preferred examples and illustration of the various definitions, in the above descriptions, which the present invention includes within the scope thereof are explained in detail as follows.

The term "lower" is intended to mean 1 to 6 carbon atoms, unless otherwise indicated.

Preferred examples of "halogen" is fluorine, chlorine, bromine and iodine.

Preferred examples of "lower alkyl" and the lower alkyl moiety may include a residue of straight and branched alkane having 1 to 6 carbon atoms such as methyl, ethyl, propyl, isopropyl, butyl, isobutyl, t-butyl, pentyl, neopentyl, hexyl and the like, and more preferably the one having 1 to 4 carbon atom(s).

Preferred examples of "lower alkoxy" may include a straight or branched one such as methoxy, ethoxy, propoxy, isopropoxy, butoxy, isobutoxy, tert-butoxy, pentyloxy, hexyloxy or the like, in which the preferable one is $C_1$-$C_4$ alkoxy and the most preferable one is methoxy or ethoxy.

Preferred example of "halo(lower)alkyl" may include those groups which are derived from the groups given above as preferred examples of the "lower alkyl" by substitution with one or more fluorine, chlorine, bromine and/or iodine optionally on one or more carbon atoms thereof. A most preferred example of such group is chloromethyl, trifluoromethyl, for instance.

Preferred examples of "lower alkylthio" may include methylthio, ethylthio, propylthio, isopropylthio, butylthio and the like, and more preferably the one having 1 to 4 carbon atoms.

Preferred examples of "lower alkylsulfonyl" may include mesyl, ethylsulfonyl, propylsulfonyl, isopropylsulfonyl, butylsulfonyl and the like, more preferably the one having 1 to 4 carbon atoms.

Preferred examples of "lower alkanoyl" may include the same as those exemplified in the explanation of "acyl" hereinafter, and more preferably the one having 1 to 4 carbon atoms.

Preferred examples of "lower alkanoyl(lower)alkenyl" may include lower alkenyl (e.g. vinyl, allyl, 1-propenyl, 1 or 2 or 3-butenyl), optional carbon atom(s) of which are substituted with lower alkanoyl (e.g. formyl, acetyl, propionyl, butyryl, isobutyryl, etc.).

Preferred examples of "lower alkylsulfonylamino" may include mesylamino, ethylsulfonylamino and the like.

Preferred examples of "heterocyclic group" may include a unsaturated 3- to 8-membered monocyclic heterocyclic group containing 1 to 4 nitrogen atoms such as pyrrolyl, pyrrolinyl, imidazolyl, pyrazolyl, pyridyl and its N-oxide, dihydropyridyl, pyrimidyl, pyrazinyl, pyridazinyl, triazolyl (e.g. 4H-1,2,4-triazolyl, 1H-1,2,3-triazolyl, 2H-1,2,3-triazolyl, etc.), tetrazolyl (e.g. 1H-tetrazolyl, 2H-tetrazolyl, etc.), and the like, a 3- to 8-membered monocyclic heterocyclic group containing at least one sulfur atom such as thienyl and the like, a 3- to 8-membered monocyclic heterocyclic group containing at least one sulfur atom and at least one nitrogen atom such as thiazolyl, isothiazolyl, thiadiazolyl and the like, a polycyclic (e.g. bicyclic) heterocyclic group containing at least one nitrogen atom such as indolyl, isoindolyl, indolizinyl, benzimidazolyl, quinolyl, isoquinolyl, quinazolinyl, imidazo[1,2-a]pyridyl and the like, a polycyclic (e.g. bicyclic) heterocyclic group containing at least one sulfur atom and at least one nitrogen atom such as benzothiazolyl, benzothiadiazolyl and the like, a polycyclic (e.g. bicyclic)heterocyclic group containing at least one oxygen atom such as benzofuranyl, isobenzofuranyl and the like, a polycyclic (e.g. bicyclic) heterocyclic group containing at least one oxygen atom and at least one nitrogen atom such as benzoxazolyl, benzoxadiazolyl and the like.

Preferred examples of "acyl" may include alkanoyl such as straight or branched lower alkanoyl [e.g. formyl, acetyl, propionyl, butyryl, isobutyryl, valeryl, isovaleryl, pivaloyl, hexanoyl, 3,3-dimethylbutyryl, etc.] or higher alkanoyl [e.g. heptanoyl, octanoyl, myristoyl, palmitoyl, stearoyl, etc.], straight or branched lower alkenoyl [e.g. acryloyl, crotonoyl, isocrotonoyl, 3-butenoyl, methacryloyl, etc.], carbamoyl, mono or di-(lower)alkylcarbamoyl [e.g. methylcarbamoyl, N,N-dimethylcarbamoyl, ethylcarbamoyl, propylcarbamoyl, isopropylcarbamoyl, butylcarbamoyl, isobutylcarbamoyl, tert-butylcarbamoyl, etc.], mono or di-lower alkylamino(lower)alkylcarbamoyl (e.g. diethylaminoethylcarbamoyl, etc.), mono or di- (lower)alkoxycarbamoyl (e.g. methoxycarbamoyl, N,N-dimethoxycarbamoyl, ethoxycarbamoyl, propoxycarbamoyl, etc.), lower alkylthio(lower)alkanoyl (e.g. methylthioacetyl, ethylthioacetyl, etc.), lower alkylsulfonyl(lower)alkanoyl (e.g. methylsulfonylacetyl, ethylsulfonylacetyl, etc.), phenyl(lower)alkanoyl (e.g. phenylacetyl, etc.), phenylcarbamoyl, phenyl(lower)alkylcarbamoyl (e.g. benzylcarbamoyl, etc.), hydroxyimino(lower)alkanoyl (e.g. 2-hydroxyiminopropionyl, etc.), S-lower alkylisothioureidocarbonyl (e.g. S-ethylisothioureidocarbonyl, etc.), lower alkylthiothiocarbonylcarbamoyl (e.g. ethylthiothiocarbonylcarbamoyl, etc.), di(lower alkylthio)-methyleneaminocarbonyl [e.g. di(ethylthio)methyleneaminocarbonyl, etc.], lower alkanoylcarbonyl (e.g. pyruvoyl, etc.), lower alkoxycarbonyl [e.g. methoxycarbonyl, ethoxycarbonyl, propoxycarbonyl, isopropoxycarbonyl, butoxycarbonyl, isobutoxycarbonyl, tert-butoxycarbonyl, pentoxycarbonyl, hexyloxycarbonyl, etc.], mono- or di- or trihalo(lower)alkanoyl [e.g. chloroformyl, chloroacetyl, bromoacetyl, trifluoroacetyl, etc.], lower alkylamino(lower)alkanoyl [e.g. methylaminoacetyl, ethylaminoacetyl, propylaminoacetyl, etc.], amino(lower)alkanoyl [e.g. aminoacetyl, aminopropionyl, etc.], aroyl [e.g. benzoyl, toluoyl, xyloyl, naphthoyl, etc.], 6-membered saturated heterocycliccarbonyl containing nitrogen atom(s) (e.g. 4-methyl-1-piperazinylcarbonyl, etc.], 6-membered unsaturated heterocyclic containing nitrogen atom(s) (lower)alkanoyl (e.g. pyridinioacetyl, etc.), and the like.

Processes for preparing the object compound (I) or its salts of this invention are explained in detail in the following.

Process 1

The object compound ($I^a$) or its salts can be prepared by reacting a compound (II) or its salts with a sulfonylating agent.

Suitable salts of the compounds ($I^a$) and (II) may include the same as those exemplified as pharmaceutically acceptable salts of the compound (I) hereinbefore.

Suitable sulfonylating agents are the corresponding sulfonic acid compounds, which are represented by the formula:$R^1SO_2$—OH wherein $R^1$ is as defined before, and reactive derivatives thereof.

As suitable said reactive derivatives, there may be mentioned acid halides, acid anhydrides and the like. Suitable examples of such reactive derivatives are acid halides such as acid chloride and acid bromide, mixed acid anhydrides with various acids [e.g. substituted phosphoric acid such as dialkyl phosphoric acid, sulfuric acid, substituted sulfonic acid such as alkanesulfonic acid, etc.], symmetric acid anhydrides and the like. The kind of such reactive derivatives can be selected depending on the kind of the group to be introduced.

The reaction is usually carried out in a conventional solvent, such as methylene chloride, chloroform, benzene, toluene, pyridine, diethyl ether, dioxane, tetrahydrofuran, acetone, acetonitrile, ethyl acetate, N,N-dimethylformamide or any other organic solvent which does not adversely affect the reaction. In case that the sulfonic acid compounds are used as sulfonylating agents in the free acid form or salt form, it is preferable to carry out the reaction in the presence of a conventional condensing agent such as N,N'-dicyclohexylcarbodiimide or the like.

The reaction temperature is not critical and the reaction can be carried out under cooling, at ambient temperature, or under warming or heating.

This reaction is preferably carried out in the presence of an inorganic base, for example an alkali metal hydroxide such as sodium hydroxide or potassium hydroxide, or an alkali metal carbonate or hydrogen carbonate such as sodium carbonate, potassium carbonate, sodium hydrogen carbonate or potassium hydrogen carbonate, or in the presence of an organic base, for example a tertiary amine such as triethylamine, pyridine or N,N-dimethylaniline.

Process 2

The object compound ($I^c$) or its salts can be prepared by reacting the compound ($I^b$) or its salts with an amine compound of the formula:

wherein $R^{10}$ is as defined before, or its salts.

Suitable salts of the compounds ($I^b$) and ($I^c$) may include the same as those exemplified as pharmaceutically acceptable salts of the compound (I) hereinbefore.

Suitable salts of the amine compound may include an inorganic acid salt (e.g. hydrochloride, hydrobromide, sulfate, etc.) and an organic acid salt (e.g. formate, acetate, 2,2,2-trifluoroacetate, p-toluenesulfonate, etc.).

This reaction may be preferably conducted in the presence of a base. Suitable base may be an inorganic base such as alkali or alkaline earth metal hydroxide (e.g. sodium hydroxide, potassium hydroxide, calcium hydroxide, etc.), alkali metal bicarbonate (e.g. sodium bicarbonate, potassium bicarbonate, etc.), alkali or alkaline earth metal carbonate (e.g. sodium carbonate, calcium carbonate, etc.), alkali metal phosphate (e.g. sodium dihydrogenphosphate, potassium dihydrogenphosphate, disodium hydrogenphosphate, dipotassium hydrogenphosphate, etc.) or an organic base such as alkali metal alkoxide (e.g. sodium methoxide, potassium ethoxide, etc.), amines (e.g. triethylamine, pyridine, lutidine, etc.).

The reaction is usually conducted in conventional manner. For example, the reaction is preferably conducted under cooling, at ambient temperature, or under warming or heating in conventional solvent which does not have an adverse influence on the reaction such as water, methanol, ethanol, propanol, N,N-dimethylformamide or an optional mixture thereof.

PROCESS 3

The object compound ($I^e$) or its salts can be prepared by reducing a compound ($I^d$) or its salts.

Suitable salts of the compounds ($I^e$) and ($I^d$) may include the same as those exemplified as pharmaceutically acceptable salts of the compound (I) hereinbefore.

In case of preparation of a compound wherein $R^{13}$ is hydroxy, the reduction is conducted by a conventional method such as a catalytic reduction; a reduction using a combination of a metal such as iron, tin or zinc and an acid such as an inorganic acid (hydrochloric acid, sulfuric acid or the like) or an organic acid (acetic acid or the like); a combination of an alloy (e.g., sodium amalgam, aluminum amalgam, etc.), a metal (e.g., zinc, tin, iron, etc.) or a salt thereof (e.g., zinc chloride, stannous chloride, ferrous chloride, etc.) and water, an alkali solution or an alcohol (e.g., methanol, ethanol, propanol or butanol); a hydrazine compound (e.g., phenyl hydrazine or hydrazine); a combination of titanium chloride and hydrochloric acid; an alkali metal borohydride such as sodium borohydride, and potassium borohydride; lithium aluminum hydride; diborane, borane; or an electrolytic reduction.

Suitable examples of catalysts for the catalytic reduction are conventional ones.

In case of preparation of a compound wherein $R^{13}$ is amino, the reduction is conducted in the presence of ammonia or its salt (e.g. ammonium acetate, etc.) and the above reducing agent.

In this reduction process, optically active compounds as an object compound ($I^e$) can be obtained by using as a reducing agent a combination of the above reducing agent and optically active ligands such as 4-anilino-3-methylamino-1-butanol, 2-amino-1,1-diphenyl-3-methylbutan-1-ol and the like.

The reaction conditions for this reduction, for example, the solvent to be used and the reaction temperature may optionally be selected in accordance with the reduction method to be used. In general, it is preferable to employ a solvent such as water, an alcohol such as methanol, ethanol and propanol, dioxane, acetonitrile, tetrahydrofuran, dimethylformamide, pyridine and the like.

The reaction temperature is not particularly limited and the reaction is usually conducted under cooling, at ambient temperature or at an elevated temperature.

PROCESS 4

The object compound ($I^g$) or its salts can be prepared by the following 2 steps:

1) the first step:

reacting a compound ($I^f$) or its salt with a halogenating agent such as halogen (e.g. chlorine, bromine, etc.), halosuccinimide (e.g. N-bromosuccinimide, N-chlorosuccinimide, etc.), sulfuryl chloride or the like.

2. the 2nd step:

reacting the resulting compound with thiourea.

The reaction of the first step is carried out under cooling, at ambient temperature, or under warming or heating in a conventional solvent which does not have an adverse influence on the reaction, such as chloroform, methylene chloride, benzene, toluene, xylene or the like.

The reaction may preferably be conducted in the presence of a reaction initiator such as benzoyl peroxide or the like.

The reaction of the 2nd step is usually carried out at ambient temperature, or under warming or heating in a conventional solvent which does not have an adverse influence on the reaction, such as methanol, ethanol, dimethylformamide, dioxane, tetrahydrofuran, chloroform or the like.

PROCESS 5

The object compound ($I^h$) or its salts can be prepared by reacting a compound ($I^{g'}$) or its salts with a sulfonylating agent.

Suitable salts of the compounds ($I^{g'}$) and ($I^h$) may include the same as those exemplified as pharmaceutically acceptable salts of the compound (I) hereinbefore.

Suitable sulfonylating agents are the corresponding sulfonic acid compounds, which are represented by the formula: $R^{14}SO_2$—OH, and reactive derivative thereof.

As suitable said reactive derivatives, there may be mentioned acid halides, acid anhydrides and the like.

This reaction is conducted substantially in the same manner as that of Process 1, and is to be referred thereto.

PROCESS 6

The object compound ($I^j$) or its salts can be prepared by reducing a compound ($I^i$) or its salts.

Suitable salts of the compounds ($I^j$) and ($I^i$) may include the same as those exemplified as pharmaceutically acceptable salts of the compound (I) hereinbefore.

Suitable reducing agents may include Raney's nickel, lithium aluminum hydride, lithium triethoxy aluminum hydride, sodium triethoxy aluminum hydride, diisobutyl aluminum hydride or the like.

The reaction is usually carried out under cooling, at ambient temperature, or under warming or heating in a solvent which does not have an adverse influence on the reaction, such as aqueous formic acid solution (in case of use of Raney's nickel), ether, tetrahydrofuran or the like.

PROCESS 7

The object compound ($I^k$) or its salts can be prepared by reacting a compound ($I^j$) or its salts with a compound of the formula: $R^{15}$—CH=P(Ph)$_3$.

Suitable salts of the compounds ($I^k$) and ($I^j$) may include the same as those exemplified as pharmaceutically acceptable salts of the compound (I) hereinbefore.

This reaction is usually carried out in a solvent such as dimethyl sulfoxide, dioxane, acetonitrile, chloroform, dichloromethane, tetrahydrofuran, dimethylformamide, ethyl acetate, or any other solvent which does not adversely affect the reaction.

The reaction temperature is not critical and the reaction is usually carried out at ambient temperature, or under warming or heating.

PROCESS 8

The object compound ($I^m$) or its salts can be prepared by reacting a compound ($I^l$) or its salts with a nitrating agent.

Suitable salts of the compounds ($I^l$) and ($I^m$) may include the same as those exemplified as pharmaceutically acceptable salts of the compound (I) hereinbefore.

Suitable examples of the nitrating agent may include nitric acid, fuming nitric acid, a mixture of nitric acid and sulfuric acid, and the like.

This reaction is conducted in the presence or absence of a solvent such as acetic acid.

The reaction temperature is not critical and the reaction is usually conducted under cooling, at ambient temperature or at an elevated temperature.

PROCESS 9

The object compound ($I^n$) or its salts can be prepared by reacting a compound (III) or its salts or its reactive derivative at carboxy with a compound (IV) or its salts.

Suitable salts of the compounds ($I^n$), (III) and (IV) may include the same as those exemplified as pharmaceutically acceptable salts of the compound (I) hereinbefore.

Suitable examples of the reactive derivative at carboxy of the compound (III) may include the same as those exemplified as reactive derivative of the sulfonic acid in Process 1.

This reaction is conducted substantially in the same manner as that of Process 1, and is to be referred thereto.

PROCESS 10

The object compound ($I^o$) or its salts can be prepared by reacting a compound (V) or its salts with a compound (VI) or its salts or its reactive derivatives at the carboxy.

Suitable salts of the compound ($I^o$) and (VI) may include the same as those exemplified as pharmaceutically acceptable salts of the compound (I) hereinbefore.

Suitable salts of the compound (V) may include an inorganic acid salt (e.g. hydrochloride, hydrobromide, sulfate, etc.) and an organic acid salt (e.g. formate, acetate, 2,2,2-trifluoroacetate, p-toluenesulfonate, etc.) and the like.

Suitable examples of the reactive derivatives at the carboxy of the compound (VI) may include the same as those exemplified as reactive derivative of the sulfonic acid in Process 1.

This reaction is conducted substantially in the same manner as that of Process 1, and is to be referred thereto.

PROCESS 11

The object compound ($I^p$) or its salts can be prepared by the following 2 steps:
1) the first step:
reacting a compound ($I^f$) or its salt with a halogenating agent such as halogen (e.g. chlorine, bromine, etc.), halosuccinimide (e.g. N-bromosuccinimide, N-chlorosuccinimide, etc.), sulfuryl chloride or the like,
2) the 2nd step:
reacting the resulting compound with 2-aminopyrimidine.

The reaction of the first step is carried out under cooling, at ambient temperature, or under warming or heating in a conventional solvent which does not have an adverse influence on the reaction, such as chloroform, methylene chloride, benzene, toluene, xylene or the like.

The reaction may preferably be conducted in the presence of a reaction initiator such as benzoyl peroxide or the like.

The reaction of the 2nd step is usually carried out at ambient temperature, or under warming or heating in a conventional solvent which does not have an adverse influence on the reaction, such as methanol, ethanol, dimethylformamide, dioxane, tetrahydrofuran, chloroform or the like.

PROCESS 12

The object compound ($I^q$) or its salts can be prepared by reacting a compound ($I^r$) or its salts with Grignard reagent.

Suitable salts of the compounds ($I^r$) and ($I^q$) may include the same as those exemplified as pharmaceutically acceptable salts of the compound (I) hereinbefore.

Suitable examples of Grignard reagent may include benzyl magnesium chloride and the like.

The reaction is usually carried out under ice-cooling or at ambient temperature, or under warming or heating in a conventional solvent which does not have an adverse influence on the reaction, such as tetrahydrofuran, diethyl ether or the like.

PROCESS 13

The object compound ($I^s$) or its salts can be prepared by halogenating a compound ($I^r$) or its salts.

Suitable salts of the compounds ($I^r$) and ($I^s$) may include the same as those exemplified as pharmaceutically acceptable salts of the compound (I) hereinbefore.

Suitable examples of a halogenating agent may include the same as those exemplified in the explanation of the first step of Process 11.

This reaction is conducted substantially in the same manner as that of the first step of Process 11, and is to be referred thereto.

PROCESS 14

The object compound ($I^t$) or its salt can be prepared by the following 2 steps:
1) the first step:
reacting a compound ($I^t$) with nitrous acid or its salts,
2) the 2nd step:
reacting the resulting compound with cuprous cyanide, a mixture of sodium cyanide and cupric sulfate, or the like.

Suitable salts of the compounds($I^t$) and ($I^t$) may include the same as those exemplified as pharmaceutically acceptable salts of the compound (I) hereinbefore.

Suitable salts of nitrous acid may include the same as those exemplified as pharmaceutically acceptable salts of the compound (I) hereinbefore.

The reaction of the first step is usually carried out under cooling or at ambient temperature in a solvent which does not have an adverse influence on the reaction, such as water, methanol, ethanol, propanol or the like.

The reaction of the 2nd step is usually carried out under ice-cooling or at room temperature, or under warming or heating in a solvent which does not have an adverse influence on the reaction, such as water, a mixture of water and dimethylformamide or tetrahydrofuran, or the like.

PROCESS 15

The object compound ($I^v$) or its salts can be prepared by reacting a compound ($I^u$) or its salts with methyl nitrite, isoamyl nitrite, nitrous acid or its salt (e.g. sodium salt), or the like.

Suitable salts of the compounds ($I^u$) and ($I^v$) may include the same as those exemplified as pharmaceutically acceptable salts of the compound (I) hereinbefore.

The reaction is usually carried out under cooling, at ambient temperature or under warming in a solvent which does not have an adverse influence on the reaction, such as diethyl ether, tetrahydrofuran, dichloromethane, or a mixture of water and said organic solvent, or the like.

PROCESS 16

The object compound ($I^w$) or its salt can be prepared by subjecting a compound ($I^v$) or its salts to hydrolysis.

Suitable salts of the compounds ($I^v$) and ($I^w$) may include the same as those exemplified as pharmaceutically acceptable salts of the compound (I) hereinbefore.

The hydrolysis is preferably conducted in the presence of an acid.

Preferred examples of the acid may include inorganic acids (e.g. hydrochloric acid, hydrobromic acid, sulfuric acid, etc.), organic acid (e.g. formic acid, acetic acid, trifluoroacetic acid, propionic acid, benzenesulfonic acid, p-toluenesulfonic acid, etc.), and acidic ion-exchange resins.

The hydrolysis is preferably conducted under comparatively mild conditions, under warming or heating, in a solvent which does not have an adverse influence on the reaction, such as water, alcohol (e.g. methanol, ethanol, propanol, etc.), acetone, N,N-dimethylformamide, tetrahydrofuran, dioxane, dimethyl sulfoxide or a mixture thereof, benzene or diethyl ether, etc. Among them, those acids which are liquid may serve also as solvents.

PROCESS 17

The object compound ($I^y$) or its salts can be prepared by oxidizing a compound ($I^x$) or its salts.

Suitable salts of the compounds ($I^x$) and ($I^y$) may include the same as those exemplified as pharmaceutically acceptable salts of the compound (I) hereinbefore.

This oxidation reaction can be carried out by a conventional method which is applied for the transformation of —S— into

for example by using an oxidizing agent such as m-chloroperbenzoic acid, perbenzoic acid, peracetic acid, ozone, hydrogen peroxide, periodic acid or the like.

This reaction is usually carried out in a solvent such as water, acetone, dioxane, acetonitrile, chloroform, dichloromethane, tetrahydrofuran, ethyl acetate or any other solvent which does not adversely affect the reaction.

The reaction temperature is not critical and the reaction is preferably carried out under cooling or at ambient temperature.

The starting compounds (II) to (VI) and their salts include novel ones and such novel compounds can be prepared, for example, according to preparations as illustrated hereinafter or a similar manner thereto.

The object compound, alkanesulfonanilide derivatives (I) and pharmaceutically acceptable salts thereof of this invention are novel compounds which have antiinflammatory activities, analgesic activities and antipyretic activities and useful as antiinflammatory (including rheumatic, arthritic) agents, analgesic agents or antipyretic agents for human being and animals.

In order to illustrate the usefulness of the object compound (I), the pharmacological test data of the representative compound of the object compound (I) are shown below.

Anti-inflammatory activity

Test 1 Effect on adjuvant arthritis in rats

Method

Ten female Sprague-Dawley rats were used per group. A dose of 0.5 mg of Mycobacterium tuberculosis (strain Aoyama B) suspended in 0.05 ml of liquid paraffin was injected subcutaneously in the right hind paw. The injection of mycobacterial adjuvant produced local inflammatory lesions (primary lesion) and then about 10 days later, secondary lesions in both the injected and uninjected paws. The difference in volumes of both paws before and after adjuvant injection was the measure of arthritis. The drug was given orally once a day for 23 consecutive days from day 1.

| Compound (Example No.) | Dose level (mg/kg) | Inhibition of Secondary Lesion (uninjected paw; %) |
|---|---|---|
| Example 1 | 1.0 | 54.2 |
|  | 3.2 | 69.8 |
| Example 2 | 10.0 | 74.2 |
| Example 4 | 10.0 | 90.1 |
| Example 7 | 3.2 | 46.3 |
| Example 12 | 10.0 | 74.3 |
| Example 13 | 10.0 | 70.3 |
| Example 14 | 10.0 | 68.9 |
| Example 24 | 10.0 | 85.1 |
| Example 31 | 10.0 | 71.7 |
| Example 45 | 10.0 | 72.4 |
| Ibuprofen | 100.0 | 54.1 |

ANALGESIC ACTIVITY

Test 2 Writhing syndrome induced by acetic acid in mice

Method:

Ten male ddY mice were used per group. Writhing syndrome was produced by an intraperitoneal injection of 20 ml/kg of 0.6% acetic acid in mice. The animals were observed from 3 to 13 minutes after acetic acid injection, and a total number of writhing episodes was recorded. The drugs were given orally 1 hour before acetic acid injection. The frequency of writhing in the treated animals was compared with that in the control animals.

| Compound (Example No.) | $ED_{50}$ (mg/kg) |
|---|---|
| Example 1 | 14.3 |
| Example 2 | 1.8 |
| Example 4 | 39.5 |
| Example 24 | 13.0 |
| Indomethacin | 1.6 |

Pharmaceutical compositions of this invention can be used in a conventional pharmaceutical forms such as powders, fine granules, granules, tablets, dragee, microcapsules, capsules, suppository, solution, suspension, emulsion, syrups and the like. If desired, diluents or disintegrators (e.g. sucrose, lactose, starch, crystalline cellulose, low-substituted hydroxypropyl cellulose, synthetic aluminum silicate, etc.) binding agents (e.g. cellulose, methylcellulose, hydroxypropylcellulose, hydroxypropylmethylcellulose, polypropylpyrrolidone, polyvinylpyrrolidone, gelatin, gum arabic, polyethyleneglycol, etc.), coloring agents, sweetening agents, lubricant (e.g. magnesium stearate, etc.) or the like, may be dispensed with said composition.

The dosage of said composition of this invention depends on the patient's age, body weight, condition, etc., and it is generally administered by the oral route at the daily dose level of 50 mg to 5 g as the object compound (I) or its pharmaceutically acceptable salts, preferably 100 mg to 500 mg on the same basis, at the interval of 1 to 3 times a day. Typical unit doses may be 50 mg, 100 mg, 200 mg, 500 mg, 1 g and the like, although these are only examples and not limitative, of course.

The following Examples are given for the purpose of illustrating this invention.

PREPARATION 1

A solution of potassium 2,4-difluorothiophenoxide (6.1 g) in methanol (30 ml) was added dropwise to a solution of 3-chloro-4-nitrobenzonitrile (5 g) in toluene (50 ml). The mixture was stirred for 5 hours at room temperature, washed with water, and concentrated to dryness. The oily residue was crystallized from a mixture of ethanol and hexane to give crystals of 3-(2,4-difluorophenylthio)-4-nitrobenzonitrile (3.6 g).

IR (Nujol):2240, 1640, 1590, 1510 cm$^{-1}$

A mixture of 3-(2,4-difluorophenylthio)-4-nitrobenzonitrile (3.6 g), sulfuric acid (3 ml) and water (3 ml) as stirred at 175° C. for 15 minutes. Water as added to the reaction mixture, and the mixture was extracted with ethyl acetate. The extract was dried over magnesium sulfate and evaporated to give crystals of 3-(2,4-difluorophenylthio)-4-nitrobenzoic acid (3.6 g).

mp:215° to 217° C.

IR (Nujol):1700, 1600, 1515 cm$^{-1}$

PREPARATION 2

A solution of 3-(2,4-difluorophenylthio)-4-nitrobenzoic acid (1.2 g) in 20% hydrogen chloride in ethanol (3 ml) was refluxed for 2 hours. The mixture was concentrated. The residue was dissolved in ethyl acetate and washed with an aqueous solution of sodium bicarbonate and water successively. The extract was evaporated and the residual oil was crystallized from a mixture of hexane and ethanol to give crystals of ethyl 3-(2,4-difluorophenylthio)-4-nitrobenzoate (1.1 g).

mp:66° to 68° C.

IR (Nujol):1725, 1600, 1515 cm$^{-1}$

A mixture of ethyl 3-(2,4-difluorophenylthio)-4-nitrobenzoate (1.1 g), iron powder (1.1 g) and ammonium chloride (0.11 g) in ethanol (10 ml) and water (5 ml) was stirred and refluxed for 1 hour. The mixture was filtered and the filtrate was concentrated under reduced pressure. The residue was dissolved in ethyl acetate, washed with water, dried and evaporated to give crystals of ethyl 4-amino-3-(2,4-difluorophenylthio)benzoate (1.1 g).

mp:68° to 71° C.

IR (Nujol):3500, 3360, 1690, 1620, 1590 cm$^{-1}$

NMR (CDCl$_3$, δ):1.37 (3 H, t, J=8 Hz), 4.35 (2 H, q, J=8 Hz), 4.83 (2 H, broad s), 6.6–8.3 (6 H, m)

PREPARATION 3

A mixture of 3-(2,4-difluorophenylthio)-4-nitrobenzoic acid (1 g) and phosphorus pentachloride (0.7 g) in benzene (10 ml) was stirred at room temperature for 30 minutes. The mixture was concentrated under reduced pressure to give a powder of 3-(2,4-difluorophenylthio)-4-nitrobenzoyl chloride (1.2 g).

IR (Nujol):1760, 1595, 1525 cm$^{-1}$

A solution of 3-(2,4-difluorophenylthio)-4-nitrobenzoyl chloride (1.2 g) in ether (8 ml) was added to a stirred mixture of 40% methylamine (2 ml), water (8 ml) and ether (5 ml) at 0° to 5° C. The mixture was stirred at the same temperature for 1 hour and at room temperature for 1 hour. The organic layer was separated, washed with water, dried and concentrated. The oily residue was crystallized from a mixture of ethyl acetate and hexane to give crystals of N-methyl-3-(2,4-difluorophenylthio)-4-nitrobenzamide (0.7 g).

mp:142° to 143° C.

IR (Nujol):3350, 1645, 1600, 1580, 1550, 1510 cm$^{-1}$

NMR (CDCl$_3$, δ):2.97 (3 H, d, J=6 Hz), 6.17 (1H, broad s), 6.8–8.4 (6 H, m)

MASS (m/e):324 (M$^+$)

PREPARATION 4

A mixture of N-methyl-3-(2,4-difluorophenylthio)-4-nitrobenzamide (0.68 g), iron powder (0.68 g) and ammonium chloride (68 mg) in ethanol (8 ml) and water (4 ml) was stirred and refluxed for 2 hours. The mixture was filtered and the filtrate was concentrated. The residue was dissolved in ethyl acetate, washed with water, dried and evaporated to give pale yellow crystals of N-methyl-4-amino-3-(2,4-difluorophenylthio)benzamide (0.78 g).

mp:72° to 75° C.

IR (Nujol):3500, 3400, 3350, 3200, 1720, 1620, 1590, 1550 cm$^{-1}$

PREPARATION 5

The following compound was obtained according to a similar manner to that of Preparation 3.

3-(2,4-Difluorophenylthio)-4-nitrobenzamide mp:170° to 172° C.

IR (Nujol):3500, 3200, 1690, 1595, 1575, 1510 cm$^{-1}$

NMR (DMSO-d$_{6,\ \delta}$):7.3–8.5 (8 H, m)

MASS (m/e):310 (M$^+$)

PREPARATION 6

The following compound was obtained according to a similar manner to that of Preparation 4.

4-Amino-3-(2,4-difluorophenylthio)benzamide

IR (Film):3480, 3360, 3200, 1650, 1600 cm$^{-1}$

PREPARATION 7

A solution of potassium 2,4-difluorothiophenoxide (5.5 g) in N,N-dimethylformamide (9 ml) was added dropwise to a solution of 4'-chloro-3'-nitroacetophenone (5 g) in toluene (50 ml). The mixture was stirred at room temperature for 2 hours, washed with water, dried and evaporated to dryness. The residue was washed with a mixture of hexane and ethanol to give crystals of 4'-(2,4-difluorophenylthio)-3'-nitroacetophenone (7.4 g).

mp:118° to 119° C.

IR (Nujol):1690, 1605, 1550, 1515 cm$^{-1}$

NMR (CDCl$_3$, δ):2.67 (3 H, s), 6.9–8.1 (5 H, m), 8.80 (1 H, d, J=2 Hz)

PREPARATION 8

The following compound was prepared according to a similar manner to that of Preparation 4.

3'-Amino-4'-(2,4-difluorophenylthio)acetophenone

PREPARATION 9

A solution of 3-chloro-4-nitrothiophenol (3.3 g) in N,N-dimethylformamide (5 ml) was added dropwise to an ice-cooled mixture of 60% sodium hydride (0.7 g) in N,N-dimethylformamide (10 ml). The mixture was stirred at 0° to 5° C. for 1 hour. To the above mixture was added dropwise methyl iodide (3.7 g) at 5° C. The mixture was stirred at room temperature for 1 hour, poured into ice-water (80 ml), and extracted with toluene. The extract was dried and evaporated. The oily residue was crystallized from a mixture of hexane and ethanol to give crystals of 3-chloro-4-nitrothioanisole (2.8 g).

IR (Nujol):1570, 1510 cm$^{-1}$

NMR (CDCl$_3$, δ):2.53 (3 H, s), 7.0–7.3 (2 H, m), 7.84 (1 H, d, J=9 Hz)

PREPARATION 10

The following compound was obtained according to a similar manner to that of Preparation 7.

2,4-Difluoro-5'-methylthio-2'-nitrodiphenylthioether
mp:124° to 125° C.
IR (Nujol):1600, 1575, 1560, 1495 cm$^{-1}$
NMR (CDCl$_3$, δ):2.25 (3 H, s), 6.4–8.2 (6 H, m)
MASS (m/e):313 (M+)

PREPARATION 11

The following compound was obtained according to a similar manner to that of Preparation 4.

2-(2,4-Difluorophenylthio)-4-methylthioaniline
IR (Nujol):3480, 3380, 1610 cm$^{-1}$

PREPARATION 12

A mixture of 3-chloro-4-nitrothioanisole (1.3 g), acetic acid (3 ml) and 30% hydrogen peroxide (1.5 ml) was stirred at 80° C. for 2 hours. The mixture was concentrated to dryness. The residue was washed with ethanol to give crystals of 3-chloro-4-nitrophenyl methyl sulfone (1.2 g).
mp:116° to 118° C.
IR (Nujol):1590, 1530 cm$^{-1}$
MASS (m/e):234 (M+), 220

The following compound was obtained according to a similar manner to that of Preparation 7.

2,4-Difluoro-5'-methylsulfonyl-2'-nitrodiphenyl-thioether
mp:152° to 153° C.
IR (Nujol):1600, 1510 cm$^{-1}$
MASS (m/e):345 (M+)

PREPARATION 13

The following compound was obtained according to a similar manner to that of Preparation 4.

2-(2,4-Difluorophenylthio)-4-methylsulfonylaniline
mp:129° to 130° C.
IR (Nujol):3500, 3400, 1615, 1585 cm$^{-1}$

PREPARATION 14

The following compound was obtained according to a similar manner to that of Preparation 7.

5-(2,4-Difluorophenylthio)-2-methyl-4-nitrobenzonitrile
mp:168° to 174° C.
IR (Nujol):2230, 1595, 1555, 1520 cm$^{-1}$
NMR (CDCl$_3$, δ):2.60 (3 H, s), 6.9–7.9 (4 H, m), 8.20 (1 H, s)

PREPARATION 15

The following compound was obtained according to a similar manner to that of Preparation 4.

4-Amino-5-(2,4-difluorophenylthio)-2-methylbenzonitrile
mp:120° to 123° C.
IR (Nujol):3480, 3370, 2220, 1610, 1600 cm$^{-1}$
NMR (CDCl$_3$, δ):2.50 (3 H, s), 4.90 (2 H, broad s), 6.6–7.3 (4 H, m), 7.75 (1 H, s)

PREPARATION 16

The following compound was obtained according to a similar manner to that of Preparation 7.

3'-(2,4-Dichlorophenylthio)-4'-nitroacetophenone
mp:90° to 92° C.
IR (Nujol):1690, 1595, 1575, 1510 cm$^{-1}$
NMR (CDCl$_3$, δ):2.48 (3 H, s), 7.3–8.0 (5 H, m), 8.33 (1 H, d, J=8 Hz)

PREPARATION 17

The following compound was obtained according to a similar manner to that of Preparation 4.

4'-Amino-3'-(2,4-dichlorophenylthio)acetophenone
mp:177° to 182° C.
IR (Nujol):3470, 3350, 1660, 1620, 1580, 1500 cm$^{-1}$
NMR (DMSOd$_{6, δ}$):2.47 (3 H, s), 6.40 (2 H, s), 6.5–8.1 (6 H, m)

PREPARATION 18

Sodium hydride (60%; 0.14 g) was added portionwise to an ice-cooled solution of 2-[3-(2,4-difluorophenylamino)-4-nitrophenyl]-2-methyl-1,3-dioxolane (1 g) in N,N-dimethylformamide. To the resulting mixture as added methyl iodide (1.7 g). The mixture was stirred at 0° C. for 30 minutes, poured into ice-water (50 ml) and extracted with ethyl acetate. The extract was washed with water, dried and evaporated. The oily residue was purified by column chromatography on silica gel (30 g) eluting with toluene to give an oil of 2-{3-[N-methyl-N-(2,4-difluorophenyl)amino]-4-nitrophenyl}-2-methyl-1,3-dioxolane (0.88 g).
IR (Film):1610, 1520 cm$^{-1}$
NMR (CDCl$_3$, δ):1.65 (3 H, s), 3.35 (3 H, s), 3 6–4 3 (4 H, m), 6.6–8.4 (6 H, m)

PREPARATION 19

A solution of 2-{3-[N-methyl-N-(2,4-difluorophenyl)amino]-4-nitrophenyl}-2-methyl-1,3-dioxolane (6.6 g) and 3N-hydrochloric acid (60 ml) in acetone (120 ml) was stirred at room temperature overnight and evaporated. The residue was dissolved in ethyl acetate, washed with water and an aqueous solution of sodium bicarbonate, and concentrated to dryness. A mixture of the residual oil (5.3 g), iron powder (5 g) and ammonium chloride (0.5 g) in ethanol (120 ml) and water (60 ml) was stirred and refluxed for 1 hour. The mixture was filtered and the filtrate was evaporated. The residue was purified by column chromatography on silica gel eluting with a mixture of toluene and ethyl acetate (20:1) to give crystals of 4'-amino-3'-[N-methyl-N-(2,4-difluorophenyl)amino]acetophenone (1.1 g).
mp:130° to 134° C.
IR (Nujol):3450, 3350, 1645, 1615, 1560, 1510 cm$^{-1}$

PREPARATION 20

A mixture of 2-(3-chloro-4-nitrophenyl)-2-methyl-1,3-dioxolane (8 g), 2,4-dichloroaniline (10.6 g), cupric oxide (0.8 g) and potassium carbonate (5.4 g) was stirred for 3 hours at 200° C. Ethyl acetate (100 ml) was added to the mixture, stirred and filtered. The filtrate was washed with water, dried and evaporated to dryness. The oil (15.5 g) was purified by column chromatography on silica gel (150 g) eluting with toluene to give an oil of 2-[3-(2,4-dichlorophenylamino)-4-nitrophenyl]-2-methyl-1,3-dioxolane (9.7 g).
IR (Film):3500, 3400, 1620, 1585, 1520 cm$^{-1}$

PREPARATION 21

The following compound was obtained according to a similar manner to that of Preparation 19.

4'-Amino-3'-(2,4-dichlorophenylamino)acetophenone
mp:176° to 179° C.
IR (Nujol):3480, 3370, 1660, 1625, 1580, 1500 cm$^{-1}$
NMR (DMSOd$_{6, δ}$):2.37 (3 H, s), 5.76 (2 H, s), 6.3–7.7 (7 H, m)

PREPARATION 22

The following compound was prepared according to a similar manner to that of Preparation 4.

4'-Acetyl-2'-aminomethanesulfonanilide
mp:130° to 150° C.
IR (Nujol):3500, 3400, 3320, 1675, 1645, 1600, 1580, 1505 cm$^{-1}$

PREPARATION 23

A mixture of 2-mercaptopyridine (1.7 g), potassium t-butoxide (1.7 g) and N,N-dimethylformamide (3 ml) in toluene (15 ml) was stirred at room temperature for 30 minutes. To the mixture was added 4'-nitro-3'-chloroacetophenone (1.5 g) and the resulting mixture was stirred overnight. Water was added and the insoluble material was filtered, washed with toluene and dried to give crystals of 4'-nitro-3'-(2-pyridylthio)acetophenone (1.1 g).

IR (Nujol):1690, 1570, 1510 cm$^{-1}$
NMR (CDCl$_3$, δ):2.34 (3 H, s), 7.0–8.6 (7 H, m)

Preparation 24

The following compound was obtained according to a similar manner to that of Preparation 4.

'-Amino-3'-(2-pyridylthio)acetophenone
IR (Nujol):3400, 3330, 3210, 1655, 1630, 1580, 1505 cm$^{-1}$

PREPARATION 25

The following compound was obtained according to a similar manner to that of Preparation 23.

4'-Nitro-3'-(2-thiazolylthio)acetophenone
mp:92° to 94° C.
IR (Nujol):1695, 1595, 1575, 1505 cm$^{-1}$
NMR (CDCl$_3$, δ):2.48 (3 H, s), 7.6–8.4 (5 H, m)
MASS (m/e):280 (M$^+$), 234

PREPARATION 26

The following compound was obtained according to a similar manner to that of Preparation 4.

4'-Amino-3'-(2-thiazolylthio)acetophenone
IR (Film):3470, 3350, 3200, 1660, 1615, 1585, 1550, 1500 cm$^{-1}$

PREPARATION 27

A mixture of 4'-acetyl-2'-(2-thiazolylthio)methanesulfonanilide (0.74 g), acetic acid (7.4 ml) and 30% hydrogen peroxide (0.67 ml) was stirred at 70° C. for 1.5 hours. The mixture was cooled to 0° C. and the precipitates were filtered, washed with ethyl acetate and dried to give colorless crystals of 4'-acetyl-2'-(2-thiazolylsulfonyl)methanesulfonanilide (0.52 g).

mp:222° to 223° C. (dec.)
IR (Nujol):1690, 1580, 1510 cm$^{-1}$
NMR (DMSOd$_6$, δ):2.65 (3 H, s), 3.88 (3 H, s), 7.1–8.6 (6 H, m)
MASS (m/e):360 (M$^+$)

PREPARATION 28

A mixture of 3'-chloro-4'-nitroacetophenone (1.5 g), 4-chlorothiophenol (1.63 g) and potassium carbonate (1.56 g) in toluene (15 ml) was stirred at 70° C. for 5 hours. Ethyl acetate and water were added, and the organic layer was separated, washed with water, dried and evaporated to dryness. The residue was washed with toluene to give yellow crystals of 3'-(4-chlorophenylthio)-4'-nitroacetophenone (1.9 g).

IR (Nujol):1695, 1590, 1575, 1510 cm$^{-1}$
NMR (CDCl$_3$, δ):2.45 (3 H, s), 7.4–8.4 (3 H, m), 7.53 (4 H, s)

PREPARATION 29

The following compound was obtained according to a similar manner to that of Preparation 4.

4'-Amino-3'-(4-chlorophenylthio)acetophenone
IR (Nujol):3470, 3350, 1660, 1620, 1580, 1500 cm$^{-1}$

PREPARATION 30

A solution of 3'-chloro-4'-nitroacetophenone (2.7 g) in toluene (50 ml) was added to a stirred solution of lithium 2-(trifluoromethyl)thiophenoxide [4.4 g; Aust. J. Chem. 32 2313 (1979)]in ether (142 ml) at 0° C. The mixture was stirred at room temperature for 2 hours and refluxed for 20 minutes. The resulting mixtures were added ethyl acetate and water, and the organic layer was washed with water, dried and evaporated. The oily residue was purified by column chromatography on silica gel (70 g) eluting with toluene to give a yellow oil of 4'-nitro-3'-[2-(trifluoromethyl)phenylthio]acetophenone (1.3 g).

IR (Film):1695, 1590, 1575, 1520 cm$^{-1}$
NMR (CDCl$_3$, δ):2.40 (3 H, s), 7.2–8.5 (7 H, m)
MASS (m/e):341 (M$^+$)

PREPARATION 31

The following compound was prepared according to a similar manner to that of Preparation 4.

4'-Amino-3'-[2-(trifluoromethyl)phenylthio]acetophenone
IR (Film):3470, 3350, 3200, 1660, 1620, 1570, 1500 cm$^{-1}$

PREPARATION 32

The following compound was obtained according to a similar manner to that of Preparation 28.

4'-Nitro-3'-(2-thienylthio)acetophenone
mp:133° to 136° C.
IR (Nujol):3100, 1695, 1595, 1575, 1510 cm$^{-1}$
NMR (DMSOd$_6$, δ):2.50 (3 H, s), 7.3–8.5 (6 H, s)
MASS (m/e):279 (M$^+$)

PREPARATION 33

The following compound was obtained according to a similar manner to that of Preparation 4.

4'-Amino-3'-(2-thienylthio)acetophenone
IR (Film):3480, 3370, 3220, 1660, 1610, 1585, 1500 cm$^{-1}$

PREPARATION 34

The following compound was obtained according to a similar manner to that of Preparation 28.

3'-(2-Chlorophenylthio)-4'-nitroacetophenone
mp:136° to 139° C.
IR (Nujol):1695, 1595, 1575, 1510 cm$^{-1}$
MASS (m/e):307 ((M$^+$)

PREPARATION 35

The following compound was prepared according to a similar manner to that of Preparation 4.

4'-Amino-3'-(2-chlorophenylthio)acetophenone
IR (Nujol):3480, 3350, 1665, 1620, 1580, 1500 cm$^{-1}$

PREPARATION 36

The following compound was obtained according to a similar manner to that of Preparation 28.

3'-(2-Methoxyphenylthio)-4'-nitroacetophenone
mp:90° to 100° C.

IR (Nujol):1695, 1590, 1580, 1510 cm$^{-1}$
MASS (m/e):303 ((M+)

PREPARATION 37

The following compound was prepared according to a similar manner to that of Preparation 4.
4'-Amino-3'-(2-methoxyphenylthio)acetophenone
IR (Nujol):3470, 3350, 1655, 1620, 1575, 1500 cm$^{-1}$

PREPARATION 38

The following compound was obtained according to a similar manner to that of Preparation 23.
30  3'-(5-Methylbenzimidazolyl-2-thio)-4'-nitroacetophenone
IR (Nujol):3120, 1695, 1590, 1520, 1495 cm$^{-1}$
MASS (m/e):327 (M+)

PREPARATION 39

The following compound was obtained according to a similar manner to that of Preparation 4.
4'-Amino-3'-(5-methylbenzimidazolyl-2-thio)acetophenone
IR (Nujol):3350, 3200, 1665, 1580, 1550 cm$^{-1}$
MASS (m/e):297 (M+)

PREPARATION 40

The following compound was obtained according to a similar manner to that of Preparation 23.
4'-Nitro-3'-(2-quinolylthio)acetophenone
IR (Nujol):1690, 1615, 1570, 1500 cm$^{-1}$
NMR (DMSOd$_6$, δ):2.64 (3 H, s), 7.2–8.5 (9 H, m)
MASS(m/e):324 (M+), 278

PREPARATION 41

The following compound was obtained according to a similar manner to that of Preparation 4.
4'-Amino-3'-(2-quinolylthio)acetophenone
IR (Nujol):3430, 3300, 3180, 1670, 1630, 1585, 1555, 1495 cm$^{-1}$

PREPARATION 42

The following compound was obtained according to a similar manner to that of Preparation 28.
4'-Nitro-3'-(pentafluorophenylthio)acetophenone
IR (Nujol):1700, 1645, 1590, 1575, 1515, 1490 cm$^{-1}$

PREPARATION 43

The following compound was obtained according to a similar manner to that of Preparation 4.
4'-Amino-3'-(pentafluorophenylthio)acetophenone
IR (Nujol):3480, 3350, 3220, 1660, 1630, 1580, 1510, 1490 cm$^{-1}$

PREPARATION 44

A solution of 3-(2,4-difluorophenylthio)-4nitrobenzoyl chloride (1 g) in tetrahydrofuran (3 ml) was added to a stirred solution of 70% ethylamine (0.5 ml) in water (5 ml) at 5° to 10° C. The mixture was stirred at the same temperature for 1 hour and at room temperature for 1 hour. Water (30 ml) was added to the reaction mixture. The precipitates were filtered, washed with water, and dried under reduced pressure to give a yellow powder of N-ethyl-3-(2,4-difluorophenylthio)-4-nitrobenzamide (0.94 g).
mp:144° to 147° C.
IR (Nujol):3300, 1630, 1595, 1570, 1550, 1510 cm$^{-1}$
NMR (CDCl$_3$, δ):1.23 (3 H, t, J=7 Hz), 3.2–3.7 (2 H, m), 6.0–6.4 (1H, m), 6.9–8.0 (5 H, m), 8.30 (1 H, d, J=8 Hz)

MASS (m/e):338 (M+)

PREPARATION 45

A mixture of N-ethyl-3-(2,4-difluorophenylthio)4-nitrobenzamide (0.92 g), iron powder (0.92 g) and ammonium chloride (92 mg) in ethanol (10 ml) and water (5 ml) was stirred and refluxed for 2 hours. The mixture was filtered and the filtrate was concentrated. The residue was dissolved in ethyl acetate, washed with water, dried, and evaporated to give an oil of N-ethyl4-amino-3-(2,4-difluorophenylthio)benzamide (0.85 g).
IR (Film):3480, 3350, 1610, 1545, 1485 cm$^{-1}$

PREPARATION 46

The following compound was obtained according to a similar manner to that of Preparation 44.
N-Isopropyl-3-(2,4-difluorophenylthio)-4-nitrobenzamide
mp:147° to 149° C.
IR (Nujol):3310, 1635, 1600, 1570, 1550, 1510 cm$^{-1}$
NMR (CDCl$_3$, δ):1.23 (6 H, d, J=6 Hz), 3.9–4.5 (1 H, m), 5.7–6.1 (1 H, m), 6.9–8.0 (5 H, m), 8.32 (1 H, d, J=8 Hz)
MASS (m/e):352 (M+)

PREPARATION 47

The following compound was obtained according to a similar manner to that of Preparation 45.
N-Isopropyl-4-amino-3-(2,4-difluorophenylthio)benzamide
mp:123° to 124° C.
IR (Nujol):3500, 3350, 1625, 1610, 1590, 1530 cm$^{-1}$

PREPARATION 48

A solution of 3-(2,4-difluorophenylthio)-4-nitrobenzoyl chloride (1 g) in tetrahydrofuran (3 ml) was added to a stirred mixture of aniline (0.306 g) and sodium bicarbonate (0.51 g) in tetrahydrofuran (2 ml) and water (5 ml) at 5° C. The mixture was stirred at 5° C. for 1 hour and at room temperature for 1 hour. Water was added to the reaction mixture and the mixture was extracted with chloroform. The extract was washed with water, dried and evaporated. The residue was washed with ethanol to give yellow crystals of N-phenyl3-(2,4-difluorophenylthio)-4-nitrobenzamide (1.1 g).
mp:175° to 177° C.
IR (Nujol):3330, 1660, 1595, 1575, 1535, 1500 cm$^{-1}$
MASS (m/e):385 (M+)

PREPARATION 49

The following compound was obtained according to a similar manner to that of Preparation 45.
N-Phenyl-4-amino-3-(2,4-difluorophenylthio)benzamide
IR (Film):3500, 3350, 1640, 1610, 1600, 1530, 1500 cm$^{-1}$
NMR (CDCl$_3$, δ):4.70 (2 H, s), 6.5–8.0 (12 H, m)

PREPARATION 50

The following compound was obtained according to a similar manner to that of Preparation 48.
N-Benzyl-3-(2,4-difluorophenylthio)-4-nitrobenzamide
mp:130° to 132° C.
IR (Nujol):3310, 1650, 1595, 1580, 1545, 1515 cm$^{-1}$
NMR (CDCl$_3$, δ):4.54 (2 H, d, J=6 Hz), 6.2–6.5 (1 H, m), 6.8–7.9 (10 H, m), 8.27 (1 H, d, J=8 Hz)
MASS (m/e):400 (M)

PREPARATION 51

The following compound was obtained according to a similar manner to that of Preparation 45.

N-Benzyl-4-amino-3-(2,4-difluorophenylthio)benzamide

IR (Film):3500, 3350, 1615, 1540, 1485 cm$^{-1}$

PREPARATION 52

The following compound was obtained in a similar manner to that of Preparation 44.

N,N-Dimethyl-3-(2,4-difluorophenylthio)-4-nitrobenzamide mp:105° to 108° C.

IR (Nujol):1640, 1595, 1570, 1510 cm$^{-1}$

NMR (CDCl$_3$, δ):2.85 (3 H, s), 3.06 (3 H, s), 6.8–8.0 (5 H, m), 8.32 (1 H, d, J=8 Hz)

MASS (m/e):338 (M+)

PREPARATION 53

The following compound was obtained according to a similar manner to that of Preparation 45.

N,N-Dimethyl-4-amino-3-(2,4-difluorophenylthio)-benzamide

IR (Film):3480, 3350, 1610, 1480 cm$^{-1}$

PREPARATION 54

A mixture of 2-(3-chloro-4-nitrophenyl)-2-methyl-1,3-dioxolane (9.8 g) and cuprous cyanide (4.0 g) in N,N-dimethylformamide (20 ml) was stirred and refluxed for 11 hours. An aqueous solution of sodium bicarbonate (200 ml) and ethyl acetate (100 ml) were added to the reaction mixture. The mixture was stirred and filtered. The filtrate was separated and the organic layer was dried and evaporated. The oily residue was purified by column chromatography on silica gel (200 g) eluting with a mixture of toluene and ethyl acetate (20:1) to give yellow plates of 2-(3-cyano-4-nitrophenyl)-2-methyl-1,3-dioxolane (4.6 g).

mp:65° to 66° C.

IR (Nujol):2230, 1590, 1530 cm$^{-1}$

NMR (CDCl$_3$, δ):1.70 (3 H, s), 3.7–4.4 (4 H, m), 7.8–8.2 (2 H, m), 8.35 (1 H, d, J=8 Hz)

PREPARATION 55

A mixture of 2-(3-cyano-4-nitrophenyl)-2-methyl-1,3-dioxolane (3.9 g), iron powder (3.9 g) and ammonium chloride (0.4 g) in ethanol (50 ml) and water (25 ml) was stirred and refluxed for 1 hour. The mixture was filtered and the filtrate was concentrated. The residue was dissolved in ethyl acetate, washed with water, dried, and evaporated to give a solid (3.1 g).

A mixture of the obtained solid, methanesulfonyl chloride (5.2 ml) and triethylamine (2 ml) in pyridine (30 ml) was stirred overnight at room temperature. The mixture was evaporated and the residue was treated with 5% sodium hydroxide solution (100 ml ) at room temperature for 3 hours. The resulting solution was washed with toluene, acidified with hydrochloric acid, and extracted with ethyl acetate. The extract was washed with water, dried and evaporated. The residue was recrystallized from a mixture of ethanol and water (1:1) to give brown needles of 4'-acetyl-2'-cyanomethanesulfonanilide (2.2 g).

mp:173° to 176° C.

IR (Nujol):3120, 2230, 1680, 1610, 1570, 1500 cm$^{-1}$

NMR (DMSOd$_{6, δ}$):2.58 (3 H, s), 3.20 (3 H, s), 7.60 (1 H, d, J=9 Hz), 8.17 (1 H, dd, J=2, 9 Hz), 8.35 (1 H, d, J=2 Hz), 9.6–11.2 (1 H, broad s)

MASS (m/e):238 (M+), 223

PREPARATION 56

A mixture of 4'-acetyl-2'-cyanomethanesulfonanilide (1.5 g) and 24% sodium hydroxide solution (15 ml) in ethanol (10 ml) was refluxed for 6 hours. The reaction mixture was acidified with hydrochloric acid. Precipitates were filtered and dried to give crystals of 5-acetyl-2-(methanesulfonamido)benzoic acid (1.5 g).

mp:196° to 201° C.

IR (Nujol):3600, 3450, 1690, 1670, 1600, 1500 cm$^{-1}$

NMR (DMSOd$_{6, δ}$):2.60 (3 H, s), 3.32 (3 H, s), 7.70 (1 H, d, J=8 Hz), 8.22 (1 H, dd, J=8, 2 Hz), 8.55 (1 H, d, J=2 Hz)

PREPARATION 57

A mixture of 2,5-dichloro-4-nitrobenzonitrile (2.5 g) and potassium 2,4-difluorothiophenoxide (2.54 g) in toluene was stirred overnight. Ethyl acetate was added and the resulting mixture was washed with water, dried and evaporated. The residue was filtered and washed with toluene to give pale brown crystals of 2-chloro-5-(2,4-difluorophenylthio)-4-nitrobenzonitrile (1.7 g).

mp:181° to 185° C.

IR (Nujol):3100, 2240, 1595, 1555, 1520, 1485 cm$^{-1}$

NMR (DMSO-d$_6$, δ):7.1–8.0 (4 H, m), 8.62 (1 H, s)

PREPARATION 58

The following compound was obtained according to a similar manner to that of Preparation 45.

4-Amino-2-chloro-5-(2,4-difluorophenylthio)benzonitrile

IR (Nujol):3500, 3370, 2220, 1620, 1585, 1485 cm$^{-1}$

PREPARATION 59

A mixture of 3-chloro-4-nitrobenzonitrile (1.6 g), thiophene-2-thiol (1.7 g) and potassium carbonate (2 g) in toluene (16 ml) was stirred overnight at 80° C. Ethyl acetate was added and the resulting mixture was washed with water, dried and evaporated. The residue was purified by column chromatography on silica gel (95 g) eluting with a mixture of hexane and toluene (1:1) to give yellow crystals of 4-nitro-3-(thiophene-2-thio)-benzonitrile (1.5 g).

IR (Nujol):3100, 2240, 1590, 1580, 1530 cm$^{-1}$

NMR (DMSO-d$_6$, δ):7.20 (1 H, d, J=2 Hz), 7.3–8.3 (4 H, m), 8.45 (1 H, d, J=8 Hz)

PREPARATION 60

The following compound was obtained according to a similar manner to that of Preparation 45.

4-Amino-3-(thiophene-2-thio)benzonitrile

IR (Film):3480, 3370, 2220, 1615, 1495 cm$^{-1}$

PREPARATION 61

The following compound was obtained according to a similar manner to that of Preparation 57.

3'-(2,4-Difluorophenylthio)-4'-nitropropiophenone

IR (Nujol):1700, 1600, 1575, 1515 cm$^{-1}$

NMR (DMSO-d$_6$, δ):1.0 (3 H, t, J=7 Hz), 2.96 (2 H, q, J=7 Hz), 7.2–8.1 (5 H, m), 8.44 (1 H, d, J=8 Hz)

Preparation 62

The following compound was prepared according to a similar manner to that of Preparation 45.

4'-Amino-3'-(2,4-difluorophenylthio)propiophenone

IR (Nujol):3490, 3360, 1670, 1620, 1585, 1485 cm$^{-1}$

PREPARATION 63

A mixture of 3'-chloro-4'-nitroacetophenone (2.4 g), potassium 2,4-difluorothiophenoxide (2.7 g), and N,Ndimethylformamide (5 ml) in xylene (50 ml) was stirred for 8 hours at room temperature. The mixture was poured into ice-water and extracted with ethyl acetate. The extract was washed with water, dried over magnesium sulfate, and concentrated under reduced pressure. The residual solid was recrystallized from ethanol to give prisms of 3'-(2,4-difluorophenylthio)-4'-nitroacetophenone (2.3 g).

mp:141° to 143° C.
IR (Nujol):1695, 1595, 1575, 1510 cm$^{-1}$
NMR (CDCl$_3$, δ):2.45 (3 H, s), 6.9–8.4 (6 H, m)

PREPARATION 64

A mixture of 3'-(2,4-difluorophenylthio)-4'-nitroacetophenone (2.3 g), iron powder (2 g), and ammonium chloride (0.2 g) in ethanol (20 ml) and water (10 ml) was refluxed with stirring for an hour. The insoluble was filtered and the filtrate was concentrated under reduced pressure. The residue was dissolved in ethyl acetate, washed with water, dried over magnesium sulfate, and concentrated to give crystals of 4'-amino-3'-(2,4-difluorophenylthio)acetophenone (2.0 g).

mp:105° to 107° C.
IR (Nujol):3450, 3340, 1665, 1620, 1575 cm$^{-1}$
NMR (CDCl$_3$, δ):2.50 (3 H, s), 6.6–7.1 (4 H, m), 7.7–8.1 (2 H, m)

PREPARATION 65

A solution of 3'-chloro-4'-nitroacetophenone (3 g), ethylene glycol (9.3 g), and p-toluenesulfonic acid monohydrate (0.5 g) in toluene (30 ml) was refluxed for 6 hours. Water formed in the reaction was removed by means of Dean Stark apparatus. The reaction mixture was washed with an aqueous solution of sodium bicarbonate, dried over magnesium sulfate, and concentrated to give an oil of 2-(3-chloro-4-nitrophenyl)-2-methyl-1,3-dioxolane (3.9 g).

IR (Film):3000, 2900, 1585, 1530 cm$^{-1}$
NMR (CDCl$_3$, δ):1.65 (3 H, s), 3.7–4.3 (4 H, m), 7.4–8.0 (3 H, m)

PREPARATION 66

A mixture of 2-(3-chloro-4-nitrophenyl)-2-methyl-1,3-dioxolane (7.9 g), 2,4-difluoroaniline (20.9 g), cupric oxide (0.8 g), and potassium carbonate (5.4 g) was stirred for 2 hours at 200° C. To the mixture were added water (50 ml) and ethyl acetate (80 ml). After stirring for 10 minutes the insoluble material was filtered. The organic layer separated from the filtrate was washed with water, dried over magnesium sulfate, and concentrated to give an oil (17 g). The oil was purified by column chromatography on silica gel (150 g) eluting with toluene to give a crude oil of 2-[3-(2,4-difluorophenylamino)-4-nitrophenyl]-2-methyl-1,3-dioxolane (10 g).

IR (Film):3500, 3400, 1620, 1580, 1510 cm$^{-1}$

PREPARATION 67

A mixture of 2-[3-(2,4-difluorophenylamino)-4-nitrophenyl]-2-methyl-1,3-dioxolane (10 g) and 3N-hydrochloric acid (20 ml) in acetone (40 ml) was stirred overnight at room temperature. The mixture was concentrated under reduced pressure. To the residue were added a saturated aqueous solution of sodium bicarbonate and ethyl acetate. The organic layer was dried and concentrated to give an oil of 3'-(2,4-difluorophenylamino)-4'-nitroacetophenone (8.5 g).

A mixture of 3'-(2,4-difluorophenylamino)-4'-nitroacetophenone (8.5 g), iron powder (8 g), and ammonium chloride (0.8 g) in ethanol (100 ml) and water (50 ml) was refluxed with stirring for 1 hour. The insoluble was filtered and the filtrate was concentrated under reduced pressure. The residue was dissolved in ethyl acetate, washed with water, dried over magnesium sulfate, and concentrated. The residual oil was purified by column chromatography on silica gel (150 g) eluting with a mixture of toluene and ethyl acetate (20:1) to give a powder of 4'-amino-3'-(2,4-difluorophenylamino)acetophenone (1.7 g).

mp:121° to 123° C.
IR (Nujol):3500, 3400, 3320, 1650, 1610, 1500 cm$^{-1}$
NMR (CDCl$_3$, δ):2.45 (3 H, s), 4.2 (2 H, broad s), 6.4–7.0 (4 H, m), 7.6–7.8 (2 H, m)
MASS (m/e):262 (M+), 247

PREPARATION 68

A solution of potassium 2,4-difluorothiophenoxide (3.6 g) in N,N-dimethylformamide (5 ml) was added dropwise to a stirred solution of 3-chloro-4-nitrobenzonitrile (3 g) in xylene (30 ml) at 5° C. The mixture was stirred overnight at room temperature, poured into ice-water (100 ml), and extracted with ethyl acetate. The extract was washed with water, dried, and concentrated to give a solid (4.7 g). The solid was recrystallized from ethanol to give orange prisms of 3-(2,4-difluorophenylthio)-4-nitrobenzonitrile (4.0 g).

mp:145° to 147° C.
IR (Nujol):2240, 1600, 1515 cm$^{-1}$
NMR (DMSO-d$_6$, δ) 7.2–8.1 (5 H, m), 8.40 (1 H, d, J=8 Hz)

PREPARATION 69

The following compound was obtained according to a similar manner to that of Preparation 64.

4-Amino-3-(2,4-difluorophenylthio)benzonitrile
mp:117° to 120° C.
IR (Nujol):3460, 3350, 2230, 1620, 1590 cm$^{-1}$
NMR (CDCl$_3$, δ):4.95 (2 H, broad s), 6.7–7.8 (6 H, m)

PREPARATION 70

Zinc chloride (7.2 g) was added portionwise to a stirred mixture of 2,4-difluorobenzoyl chloride (17 g) and 4-ethylaniline (5.3 g) at 180° C. The mixture was stirred for 2.5 hours at 200° C. and cooled to 120° C. To the mixture was added 3N hydrochloric acid (50 ml) and the resulting mixture was refluxed for 1.5 hours, then the supernatant was decanted out. The above procedure was repeated three times. 75% Sulfuric acid (40 ml) was added and the reaction mixture was stirred and heated at 140° C. for 2 hours. The reaction mixture was poured into ice (500 ml) and extracted with dichloromethane. The organic layer was washed with 3N hydrochloric acid (200 ml), 3N sodium hydroxide (200 ml) and water, dried, and evaporated. The oily residue (5.7 g) was purified by column chromatography on silica gel (170 g) eluting with toluene to give crystals of 2-amino-5-ethyl-2',4'-difluorobenzophenone (3.5 g).

mp:42° to 46° C.
IR (Nujol):3470, 3360, 1630, 1590, 1550 cm$^{-1}$
NMR (CDCl$_3$, δ):1.10 (3 H, t, J=7.5 Hz), 2.45 (2 H, q, J=7.5 Hz), 6.2 (2 H, s), 6.68 (1 H, d, J=8 Hz), 6.8–7.6 (5 H, m)

PREPARATION 71

A mixture of 4-acetyl-2-(2,4-difluorobenzoyl)acetanilide (4.2 g) and concentrated hydrochloric acid (10 ml) in ethanol (30 ml) was refluxed for 5 hours. The mixture was concentrated and the residue was dissolved in ethyl acetate (100 ml). The solution obtained was washed with an aqueous solution of sodium bicarbonate, dried and evaporated to give crystals of 5-acetyl-2-amino-2',4'-difluorobenzophenone (3.6 g).

mp:161° to 164° C.
IR (Nujol):3450, 3330, 1670, 1610, 1550 cm$^{-1}$
NMR (CDCl$_3$, δ):2.42 (3 H, s), 6.7–8.1 (8 H, m)

PREPARATION 72

A mixture of 2-(2,4-difluorobenzoyl)-4-ethylacetanilide (3.1 g), magnesium oxide (1.0 g), nitric acid (3.4 ml) and potassium permanganate (4.0 g) in water (300 ml) was stirred at 60° C. for 9 hours. The mixture was cooled. Ethyl acetate (150 ml) and sodium bisulfite (15 g) were added. The mixture was stirred for 1 hour and the insoluble was filtered off. The filtrate was separated and the organic layer was dried and evaporated to dryness (2.9 g). The residue was purified by column chromatography on silica gel (80 g) eluting with a mixture of toluene and ethyl acetate (20:1) to give needles of 4-acetyl-2-(2,4-difluorobenzoyl)acetanilide (2.3 g).

mp:132° to 134° C.
IR (Nujol):3270, 1710, 1670, 1650, 1610, 1590, 1520 cm$^{-1}$
NMR (CDCl$_3$, δ):2.29 (3 H, s), 2.52 (3 H, s), 6.8–7.7 (3 H, m), 8.1–8.3 (2 H, m), 8.89 (1 H, d, J=10 Hz), 11.3 (1 H, s)

PREPARATION 73

A mixture of 3-chloro-4-nitrobenzonitrile (5 g), 2,4-difluoroaniline (17.7 g), cupric oxide (0.5 g) and potassium carbonate (4.5 g) was stirred for 5 hours at 200° C. To the mixture were added water (100 ml) and ethyl acetate (200 ml). The organic layer was separated, washed with 3N hydrochloric acid and water, dried, and evaporated to dryness. The oil (10 g) was purified by column chromatography on silica gel (200 g) eluting with toluene to give red crystals of 3-(2,4-difluorophenylamino)-4-nitrobenzonitrile (3.5 g).

mp:105° to 108° C.
IR (Nujol):3350, 2230, 1620, 1580, 1510 cm$^{-1}$
NMR (CDCl$_3$, δ):6.9–8.6 (6 H, m), 9.25 (1 H, broad s)

PREPARATION 74

A mixture of 3-(2,4-difluorophenylamino)-4-nitrobenzonitrile (3.5 g), iron powder (3.5 g) and ammonium chloride (0.35 g) in ethanol (50 ml) and water (25 ml) was refluxed for 1 hour. The insoluble material was filtered and the filtrate was concentrated. The residue was dissolved in ethyl acetate, washed with water, dried and evaporated to dryness. The residual oil (3 g) was purified by column chromatography on silica gel (100 g) eluting with a mixture of toluene and ethyl acetate to give a powder of 4-amino-3-(2,4-difluorophenylamino)benzonitrile (1.2 g).

mp:103° to 106° C.
IR (Nujol):3520, 3420, 3360, 2210, 1620, 1515 cm$^{-1}$
NMR (CDCl$_3$, δ):4.1 (2 H, broad s), 5.1 (1 H, broad s), 6.5–7.1 (4 H, m), 7.3–7.5 (2 H, m)

PREPARATION 75

A mixture of 2-amino-5-ethyl-2',4'-difluorobenzophenone (3.4 g) and acetic anhydride (1.6 g) in pyridine (20 ml) was stirred overnight at room temperature. Water (5 ml) was added and the mixture was concentrated under reduced pressure. The residue was dissolved in ethyl acetate (50 ml), washed with 2N hydrochloric acid and a saturated aqueous solution of sodium bicarbonate, dried and concentrated. The residue was purified by column chromatography on silica gel (90 g) eluting with a mixture of toluene and ethyl acetate (40:1) to give needles of 2-(2,4-difluorobenzoyl)-4-ethylacetanilide (3.3 g).

mp:97° to 99° C.
IR (Nujol):3300, 1690, 1640, 1590, 1520 cm$^{-1}$
NMR (CDCl$_3$, δ):1.16 (3 H, t, J=7.5 Hz), 2.25 (3 H, s), 2.58 (2 H, q, J=7.5 Hz), 6.8–7.7 (5 H, m), 8.68 (1 H, d, J=8.5 Hz), 11.1 (1 H, s)

PREPARATION 76

A mixture of 2,4-difluorobenzoyl chloride (88.3 g) and 4-nitroaniline (32.9 g) was heated at 180° C. for 25 minutes. Zinc chloride (39 g) was added portionwise to the resulting mixture. The mixture was stirred for 2.5 hours at 195° C. and cooled to 130° C. To the mixture was added 3N hydrochloric acid (100 ml) and the resulting mixture was refluxed for 2 hours, then the supernatant was decanted out. 75% Sulfuric acid was added to the residue and the mixture was stirred at 130° C. for 2 hours. The reaction mixture was poured into ice and extracted with dichloromethane. The organic layer was washed with 3N hydrochloric acid (600 ml), 3N sodium hydroxide (1 l), and water successively, dried, and evaporated. The solid residue (15 g) was recrystallized from ethanol to give crystals of 2-amino-5-nitro-2',4'-difluorobenzophenone (6.3 g).

mp:169° to 171° C.
IR (Nujol):3470, 3330, 1610, 1590, 1550, 1500 cm$^{-1}$
NMR (DMSO-d$_6$, δ):6.98 (1 H, d, J=9 Hz), 7.1–8.2 (5 H, m), 8.40 (2 H, s)

PREPARATION 77

A mixture of 3-(2,4-difluorophenylamino)-4-nitrobenzonitrile (6.9 g) and 24% sodium hydroxide solution (50 ml) in ethanol (50 ml) was refluxed for 2 hours. The mixture was poured into ice-water (400 ml) and acidified with hydrochloric acid. The precipitate was filtered and washed with water to give red brown needles of 3-(2,4-difluorophenylamino)-4-nitrobenzoic acid (7.1 g).

mp:201° to 203° C.
IR (Nujol):3360, 1700, 1625, 1610, 1580, 1510 cm$^{-1}$
NMR (DMSO-d$_6$, δ):7.0–8.9 (6 H, m), 9.30 (1 H, s), 13.2 (1 H, broad s)

PREPARATION 78

A mixture of 3-(2,4-difluorophenylamino)-4-nitrobenzoic acid (3.5 g) in thionyl chloride (20 ml) was stirred and refluxed for 30 minutes. The mixture was concentrated to give a solid residue.

A solution of the residue (3.8 g) in tetrahydrofuran (20 ml) was added dropwise to a stirred mixture of ammonia water (28%; 10 ml) and tetrahydrofuran (10 ml) at 5° to 10° C. The mixture was stirred overnight at room temperature. The reaction mixture was poured into ice-water (300 ml) and adjusted to pH 3 with hydrochloric acid. The insoluble was filtered and washed with water to give yellow brown crystals of 3-(2,4-difluorophenylamino)-4-nitrobenzamide (2.9 g).

mp:202° to 207° C.
IR (Nujol):3400, 3200, 1660, 1620, 1575, 1510 cm$^{-1}$

NMR (DMSO-d$_6$, δ):7.1–8.4 (8 H, m), 9.25 (1 H, s)

PREPARATION 79

The following compound was obtained according to a similar manner to that of Preparation 45.

4-Amino-3-(2,4-difluorophenylamino)benzamide mp:123° to 125° C.

IR (Nujol):3525, 3420, 3350, 3210, 1650, 1620, 1600, 1570, 1520 cm$^{-1}$

NMR (CDCl$_3$-CD$_3$OD, δ):3.74 (5 H, s), 6.3–7.0 (4 H, m), 7.3–7.6 (2 H, m)

MASS (m/e):263 (M+)

PREPARATION 80

The following compound was obtained according to a similar manner to that of Preparation 78.

N-Methyl-3-(2,4-difluorophenylamino)-4-nitrobenzamide mp:153° to 158° C.

IR (Nujol):3360, 1650, 1620, 1580, 1550, 1510 cm$^{-1}$

NMR (DMSO-d$_6$, δ):2.74 (3 H, d, J=5 Hz), 7.0–8.9 (7 H, m), 9.30 (1 H, s)

PREPARATION 81

The following compound was obtained according to a similar manner to that of Preparation 45.

N-Methyl-4-amino-3-(3,4-difluorophenylamino)benzamide

IR (Film):3350, 1620, 1510 cm$^{-1}$

PREPARATION 82

A mixture of 4'-amino-3'-(2,4-difluorophenylthio)acetophenone (2 g), pyridine (0.623 g) and iodobenzene dichloride (2.7 g) in tetrahydrofuran (20 ml) was stirred for 1.5 hours at 0° to 5° C. The mixture was concentrated to dryness. The residue was dissolved in ethyl acetate, washed with water and an aqueous solution of sodium hydrogensulfite successively, dried, and evaporated. The solid residue was washed with a mixture of hexane and ethanol to give 4'-amino-3'-chloro-5'-(2,4-difluorophenylthio)acetophenone (1.7 g).

IR (Nujol):3460, 3330, 1675, 1600, 1545, 1480 cm$^{-1}$

NMR (CDCl$_3$, δ):2.47 (3 H, s), 5.22 (2 H, broad s), 6.6–7.3 (3 H, m), 7.8–8.0 (2 H, m)

PREPARATION 83

The following compound was obtained according to a similar manner to that of Preparation 59.

4'-Nitro-3'-(phenylthio)acetophenone

IR (Nujol):1690, 1595, 1575, 1510 cm$^{-1}$

PREPARATION 84

The following compound was prepared according to a similar manner to that of Preparation 45.

4'-Amino-3'-(phenylthio)acetophenone

IR (Nujol):3480, 3370, 3200, 1660, 1615, 1580, 1505 cm$^{-1}$

PREPARATION 85

A mixture of 5-mercapto-1-methyltetrazole (10.5 g), potassium t-butoxide (10.2 g) and N,N-dimethylformamide (18 ml) in xylene (90 ml) was stirred at room temperature for 30 minutes. To the mixture was added 4'-nitro-3'-chloroacetophenone (9 g), and the resulting mixture was stirred at 100° C. for 1 hour and refluxed for 5 hours. The mixture was dissolved in ethyl acetate, washed with water, dried over magnesium sulfate, and evaporated to dryness. The residual solid was filtered and washed with a mixture of toluene and ethyl acetate (1:1) to give pale brown crystals of 3'-(1-methyltetrazole-5-thio)-4'-nitroacetophenone (4.4 g).

mp:111° to 115° C.

IR (Nujol):1695, 1595, 1580, 1515 cm$^{-1}$

NMR (DMSO-d$_6$, δ):2.56 (3 H, s), 4.10 (3 H, s), 7.39 (1 H, d, J=2 Hz), 8.10 (1 H, dd, J=8, 2 Hz), 8.48 (1 H, d, J=8 Hz).

MASS (m/e):279 (M+).

PREPARATION 86

The following compound was obtained according to a similar manner to that of Preparation 45.

4'-Amino-3'-(1-methyltetrazole-5-thio)acetophenone.

mp:186° to 188° C.

IR (Nujol):3460, 3350, 1670, 1630, 1590, 1500 cm$^{-1}$.

MASS (m/e):249 (M+)

PREPARATION 87

The following compound was obtained according to a similar manner to that of Preparation 44.

N-(N,N-Diethylaminoethyl)-3-(2,4-difluorophenylthio)4-nitrobenzamide.

IR (Film):3350, 1660, 1645, 1595, 1575, 1510 cm$^{-1}$.

NMR (CDCl$_3$, δ):1.10 (6 H, t, J=7 Hz), 2.67 (4 H, q, J=7 Hz), 2.75 (2 H, t, J=6 Hz), 3.3–3.7 (2 H, m), 6.5–7.1 (4 H, m), 7.2–8.0 (3 H, m).

PREPARATION 88

The following compound was obtained according to a similar manner to that of Preparation 45.

N-(N,N-Diethylaminoethyl)-4-amino-3-(2,4-difluorophenylthio)-benzamide.

IR (Film):3460, 3325, 3200, 1620, 1595, 1540, 1480 cm$^{-1}$.

EXAMPLE 1

A mixture of 4'-amino-3'-(2,4-difluorophenylthio)acetophenone (2.0 g) and methanesulfonyl chloride (1.0 g) in pyridine (20 ml) was stirred overnight at room temperature. The mixture was poured into cold diluted hydrochloric acid and extracted with ethyl acetate. The extract was washed with water, dried, and concentrated under reduced pressure. The residue was recrystallized from ethanol to give yellow crystals of 4'-acetyl-2'-(2,4-difluorophenylthio)methanesulfonanilide (1.3 g).

mp:114° to 117° C.

IR (Nujol):3250, 1680, 1595, 1490 cm$^{-1}$

NMR (CDCl$_3$, δ):2.55 (3 H, s), 3.02 (3 H, s), 6.7–8.3 (7 H, m)

MASS (m/e):357 (M+), 278, 43 (base peak)

EXAMPLE 2

A mixture of 4'-amino-3'-(2,4-difluorophenylamino)acetophenone (1.7 g) and methanesulfonyl chloride (0.9 g) in pyridine (17 ml) was stirred for 4 hours at room temperature. Pyridine was evaporated and the residue was stirred with an aqueous solution of sodium hydroxide (5%) for 30 minutes. The solution was washed with toluene, acidified to pH 3 with hydrochloric acid, and extracted with ethyl acetate. The extract was washed with an aqueous solution of sodium bicarbonate, dried, and concentrated under reduced pressure. The syrupy residue (1.8 g) was crystallized from ethanol to give pale yellow crystals of 4'-acetyl-2'-(2,4-difluorophenylamino)methanesulfonanilide (1.3 g).

mp:113° to 115° C.

IR (Nujol):3420, 3150, 1670, 1610 cm

NMR (CDCl$_3$, δ):2.51 (3 H, s), 3.08 (3 H, s), 5.84 (1 H, broad s), 6.6–7.8 (7 H, m)
MASS (m/e):340 (M+), 261, 241

EXAMPLE 3

The following compound was prepared according to a similar manner to that of Example 2.

4'-Cyano-2'-(2,4-difluorophenylthio)methanesulfonanilide
mp:134° to 135° C.
IR (Nujol):3240, 2240, 1595, 1485 cm$^{-1}$
NMR (CDCl$_3$, δ):3.05 (3 H, s), 6.7–8.0 (7 H, m)
MASS (m/e):340 (M+), 261, 241

EXAMPLE 4

Sodium borohydride (0.2 g) was added portionwise to a solution of 4'-acetyl-2'-(2,4-difluorophenylthio)methanesulfonanilide (1.55 g) in methanol (30 ml) at 15° C. The mixture was stirred overnight at room temperature, treated with acetic acid, and concentrated under reduced pressure. The residue was dissolved in ethyl acetate, washed with an aqueous solution of sodium bicarbonate, dried, and concentrated. The residual oil (1.6 g) was purified by column chromatography on silica gel (50 g) eluting with a mixture of toluene and ethyl acetate (4:1). The purified product was recrystallized from a mixture of ethanol and water (2:1) to give crystals of 2'-(2,4-difluorophenylthio)-4'-(1-hydroxyethyl)methanesulfonanilide (1.03 g).
mp:118° to 120° C.
IR (Nujol):3450, 3100, 1595, 1485 cm$^{-1}$
NMR (CDCl$_3$, δ):1.43 (3 H, d, J=6 Hz), 1.87 (1 H, s), 2.92 (3 H, s), 4.85 (1 H, q, J=6 Hz), 6.7–7.8 (7 H, m)
MASS (m/e):359 (M+), 344, 341, 280

EXAMPLE 5

A mixture of 4'-acetyl-2'-(2,4-difluorophenylthio)methanesulfonanilide methanesulfonanilide (1.16 g), semicarbazide hydrochloride (0.4 g), and pyridine (0.29 ml) in ethanol (15 ml) was stirred and refluxed for 2 hours. The mixture was concentrated under reduced pressure. The residue was triturated with water, filtered, washed with water, and recrystallized from methanol to give a powder of 3'-(2,4-difluorophenylthio)-4'-methanesulfonamidoacetophenone semicarbazone (0.92 g).
mp:201° to 203° C. (dec.)
IR (Nujol):3520, 3400, 1675, 1600, 1570 cm$^{-1}$
NMR (DMSO-d$_6$, δ):2.05 (3 H, s), 3.05 (3 H, s), 6.33 (2 H, s), 7.0–8.0 (6 H, m), 9.39 (2 H, s)
MASS (m/e):414 (M+), 397, 371, 242

EXAMPLE 6

A mixture of 5-acetyl-2-amino-2',4'-difluorobenzophenone (3.3 g), methanesulfonyl chloride (5.5 ml) and pyridine (1 ml) in benzene (30 ml) was refluxed for 4 hours. The reaction mixture was poured into icewater (100 ml) and extracted with ethyl acetate (100 ml). The extract was washed with an aqueous solution of sodium bicarbonate, dried and concentrated. The residue (5 g) was purified by column chromatography on silica gel (120 g) eluting with a mixture of toluene and ethyl acetate (20:1), and recrystallized from ethanol to afford yellow crystals of 4'-acetyl-2'-(2,4-difluorobenzoyl)methanesulfonanilide (1.5 g).
mp:114° to 117° C.
IR (Nujol):3100, 1690, 1640, 1615, 1600, 1500 cm$^{-1}$
NMR (CDCl$_3$, δ):2.55 (3 H, s), 3.21 (3 H, s), 6.7–8.3 (6 H, m), 10.95 (1 H, s)
MASS (m/e):353 (M+), 338, 255, 240

EXAMPLE 7

Sodium borohydride (0.2 g) was added portionwise to a solution of 4'-acetyl-2'-(2,4-difluorophenylamino)methanesulfonanilide (1.5 g) in methanol (15 ml) at 5° to 10° C. The mixture was stirred for 10 hours at room temperature, treated with acetic acid, and concentrated. The residue was triturated with water and filtered. The solid (1.6 g) was recrystallized from a mixture of ethanol and ethyl acetate to give colorless needles of 2'-(2,4-difluorophenylamino)-4'-(1-hydroxyethyl)methanesulfonanilide (0.89 g).
mp:192° to 193° C.
IR (Nujol):3450, 3150, 1610, 1580, 1530, 1500 cm$^{-1}$
NMR (DMSO-d$_6$, δ):1.25 (3 H, d, J=7 Hz), 2.94 (3 H, s), 4.4–4.7 (1 H, m), 5.07 (1 H, d, J=3.5 Hz), 6.8–7.5 (7 H, m), 9.0 (1 H, s)

EXAMPLE 8

A mixture of 4-amino-3-(2,4-difluorophenylamino)benzonitrile (1.2 g) and methanesulfonyl chloride (0.45 ml) in pyridine (12 ml) was stirred for 4 hours at room temperature. Pyridine was evaporated and the residue was stirred with an aqueous solution of sodium hydroxide (5%; 40 ml) for 10 minutes. The solution was washed with toluene, acidified to pH 3 with hydrochloric acid, and extracted with ethyl acetate. The extract was washed with water, dried and evaporated to dryness. The residue (1.4 g) was recrystallized from ethanol to give colorless prisms of 4'-cyano-2'-(2,4-difluorophenylamino)methanesulfonanilide (1.2 g).
mp:167° to 169° C.
IR (Nujol):3350, 3260, 2240, 1600, 1580, 1515 cm$^{-1}$
NMR (DMSO-d$_6$, δ):3.10 (3 H, s), 6.9–7.6 (7 H, m), 9.47 (1 H, s)
MASS (m/e):323 (M+), 244, 224

EXAMPLE 9

A solution of m-chloroperbenzoic acid (80%; 0.76 g) in dichloromethane (12 ml) was added dropwise to a stirred solution of 4'-acetyl-2'-(2,4-difluorophenylthio)methanesulfonanilide (1.2 g) in dichloromethane (12 ml) at 5° to 10° C. The solution was stirred for 1 hour at the same temperature, washed with a saturated aqueous solution of sodium bicarbonate, dried over magnesium sulfate, and concentrated. The oily residue (0.9 g) was crystallized from ethanol to give crystals of 4'-acetyl-2'-(2,4-difluorophenylsulfinyl)methanesulfonanilide (0.73 g).
mp:151° to 152° C.
IR (Nujol):3100, 1685, 1600, 1500 cm$^{-1}$
NMR (DMSO-d$_6$, δ):2.60 (3 H, s), 3.08 (3 H, s), 7.1–7.8 (7 H, m)
MASS (m/e):373 (M+), 357

EXAMPLE 10

To a stirred solution of 4'-acetyl-2'-(2,4-difluorophenylthio)methanesulfonanilide (1.2 g) in acetic acid (7 ml) was added dropwise 30% hydrogen peroxide (1 ml). The mixture was stirred for 1 hour at 70° C., cooled to room temperature, and treated with an aqueous solution of sodium bisulfite to decompose excess hydrogen peroxide. The resulting mixture was poured into water (50 ml) and the precipitates were filtered, washed with water and dried. The crude crystals (1.3 g) were recrystallized from a mixture of ethanol and ethyl acetate (1:1)

to give pure needles of 4'-acetyl-2'-(2,4-difluorophenyl-sulfonyl)methanesulfonanilide (1.1 g).
mp:183° to 184° C.
IR (Nujol):3280, 1690, 1600, 1495 cm$^{-1}$
NMR (DMSO-d$_6$, δ):2.60 (3 H, s), 3.25 (3 H, s), 7.2–8.5 (7 H, m)
MASS (m/e):389 (M+), 374

EXAMPLE 11

A mixture of ethyl 4-amino-3-(2,4-difluorophenylthio)benzoate (1.1 g) and methanesulfonyl chloride (0.93 g) in pyridine (5 ml) was stirred at 60° C. for 2 hours. The reaction mixture was evaporated. The residue was dissolved in methanol and treated with potassium hydroxide (2 g). The mixture was concentrated and the residue was dissolved in water and washed with chloroform. The aqueous layer was acidified with hydrochloric acid and extracted with ethyl acetate. The extract was washed with water, dried and evaporated. The solid residue was recrystallized from ethanol to give 3-(2,4-difluorophenylthio)-4-(methanesulfonamido)benzoic acid (0.66 g).
mp:185° to 187° C.
IR (Nujol):3240, 1690, 1600 cm$^{-1}$
NMR (DMSO-d$_6$, δ):3.17 (3 H, s), 7.1–8.0 (7 H, m)
MASS (m/e):359 (M+)

EXAMPLE 12

The following compound was obtained according to a similar manner to that of Example 11.
N-Methyl-3-(2,4-difluorophenylthio)-4-(methanesulfonamido)benzamide
mp:154° to 155° C.
IR (Nujol): 3400, 3325, 1630, 1600, 1550 cm$^{-1}$
NMR (CDCl$_3$, δ):3.00 (3 H, d, J=6 Hz), 3.00 (3 H, s), 6.2–6.5 (1 H, m), 6.7–8.1 (7 H, m)
MASS (m/e):372 (M+), 342

EXAMPLE 13

A mixture of 4-amino-3-(2,4-difluorophenylthio)benzamide (0.82 g), methanesulfonyl chloride (0.64 g) and triethylamine (0.6 g) in dichloromethane (10 ml) was stirred for 2 hours at room temperature. The reaction mixture was evaporated. To the residue were added methanol (10 ml) and potassium hydroxide (0.6 g). The mixture was kept overnight and evporated. The residue was treated with diluted hydrochloric acid and extracted with ethyl acetate. The extract was washed with water, dried and concentrated. The residue obtained was recrystallized from ethanol to give 3-(2,4-difluorophenylthio)-4-(methanesulfonamido)benzamide (0.54 g).
mp:176° to 178° C.
IR (Nujol):3420, 3250, 3200, 1660, 1615 cm$^{-1}$
NMR (DMSO-d$_6$, δ):3.13 (3 H, s), 7.1–8.1 (8 H, m), 9.50 (1 H, s)
MASS (m/e):358 (M+)

EXAMPLE 14

A mixture of 4'-acetyl-2'-(2,4-difluorophenylthio)methanesulfonanilide (0.9 g), methoxylamine hydrochloride (0.21 g) and pyridine (0.2 g) in ethanol (15 ml) was refluxed for 4 hours. The mixture was concentrated under reduced pressure, and the residue was triturated with water to give a powder. The powder was recrystallized from ethanol to give 2'-(2,4-difluorophenylthio)-4'-[1-(methoxyimino)ethyl]methanesulfonanilide (0.8 g).
mp:110° to 111° C.
IR (Nujol):3300, 1600, 1490 cm$^{-1}$
NMR (DMSO-d$_6$, δ):2.07 (3 H, s), 3.13 (3 H, s), 3.87 (3 H, s), 7.0–7.8 (6 H, m), 9.42 (1 H, s)
MASS (m/e):386 (M+), 307

EXAMPLE 15

The following compound was obtained according to a similar manner to that of Example 14.
2'-(2,4-Difluorophenylthio)-4'-[1-(hydroxyimino)ethyl]methanesulfonanilide
mp:196° to 197° C.
IR (Nujol):3250, 1595, 1485 cm$^{-1}$
NMR (DMSO-d$_6$, δ):2.07 (3 H, s), 3.12 (3 H, s), 7.1–7.8 (6 H, m), 9.43 (1 H, s), 11.10 (1 H, s)
MASS (m/e):372 (M+), 356

EXAMPLE 16

A solution of bromine (0.81 g) in chloroform (5 ml) was added dropwise to a stirred solution of 4'-acetyl2'-(2,4-difluorophenylthio)methanesulfonanilide (1.8 g) and benzoyl peroxide (8 mg) in chloroform (20 ml). After stirring for 1 hour at room temperature, the mixture was washed with water and an aqueous solution of sodium bisulfite successively. The organic layer was dried and concentrated to give 4'-bromoacetyl-2'(2,4-difluorophenylthio)methanesulfonanilide.
IR (Nujol):3290, 1680, 1590, 1485 cm$^{-1}$

EXAMPLE 17

A mixture of 4'-bromoacetyl-2'-(2,4-difluorophenylthio)methanesulfonanilide and thiourea (0.58 g) in methanol (15 ml) was refluxed for 1 hour, and then cooled. The precipitates were filtered, washed with ethanol and dried to give crystals of 4'-(2-amino-4-thiazolyl)-2'-(2,4-difluorophenylthio)methanesulfonanilide hydrobromide (1.9 g).
mp:134° to 137° C.
IR (Nujol):3460, 3400, 3300, 3100, 1625, 1600, 1570 cm$^{-1}$
NMR (DMSO-d$_6$, δ):3.14 (3 H, s), 7.15 (1 H, s), 7.1–8.1 (8 H, m), 9.50 (1 H, s)
MASS (m/e):413 (M+), 334

EXAMPLE 18

The following compound was obtained according to a similar manner to that of Example 13.
5'-Acetyl-2'-(2,4-difluorophenylthio)methanesulfonanilide
mp:131° to 132° C.
IR (Nujol):3250, 1675, 1595 cm$^{-1}$
NMR (CDCl$_3$, δ):2.60 (3 H, s), 3.07 (3 H, s), 6.8–8.3 (7 H, m)
MASS (m/e):357 (M+)

EXAMPLE 19

A mixture of 5'-acetyl-2'-(2,4-difluorophenylthio)methanesulfonanilide (1 g) and nitric acid (248 mg) in acetic acid (5 ml) was stirred at 80° C. for 1 hour. The reaction mixture was evaporated to dryness. The residue was washed with ethanol to give yellow crystals of 5'-acetyl-2'-(2,4-difluorophenylthio)-4'-nitromethanesulfonanilide (0.96 g).
mp:169° to 170° C.
IR (Nujol):3240, 1710, 1600, 1560, 1520 cm$^{-1}$
NMR (CDCl$_3$, δ):2.57 (3 H, s), 3.13 (3 H, s), 6.8–7.6 (3 H, m), 7.64 (1 H, s), 8.0 (1 H, broad s), 8.27 (1 H, s)
MASS (m/e):402 (M+)

EXAMPLE 20

The following compound was obtained according to a similar manner to that of Example 13.

2'-(2,4-Difluorophenylthio)-4'-methylthiomethanesulfonanilide mp:86° to 88° C.
IR (Nujol):3250, 1600, 1590 cm$^{-1}$
NMR (CDCl$_3$, δ):2.47 (3 H, s), 2.95 (3 H, s), 6.7–7.8 (7 H, m)
MASS (m/e):361 (M+)

EXAMPLE 21

The following compound was obtained according to a similar manner to that of Example 13.

2'-(2,4-Difluorophenylthio)-4'-methylsulfonylmethanesulfonanilide mp:179° to 180° C.
IR (Nujol):3250, 1590, 1480 cm$^{-1}$
NMR (DMSO-d$_6$, δ):3.20 (6 H, s), 7.1–8.1 (6 H, m), 9.82 (1 H, s)
MASS (m/e):392

EXAMPLE 22

Methanesulfonyl chloride (2.2 ml) was added dropwise to an ice-cooled solution of 4-amino-5-(2,4-difluorophenylthio)-2-methylbenzonitrile (3.9 g) and triethylamine (3.9 ml) in pyridine (40 ml). The mixture was stirred overnight at room temperature and concentrated to dryness. To the residue were added pyridine (10 ml) and 5% aqueous solution of sodium hydroxide (50 ml). The resulting mixture was stirred for 2 hours and washed with toluene (50 ml). The aqueous layer was acidified with hydrochloric acid, and the precipitates obtained were recrystallized from a mixture of ethanol and ethyl acetate to give a pale brown powder of 4'-cyano-2'-(2,4-difluorophenylthio)-5'-methylmethanesulfonanilide (2.6 g).

mp:137° to 139° C.
IR (Nujol):3230, 2220, 1600, 1550 cm$^{-1}$
NMR (CDCl$_3$, δ):2.52 (3 H, s), 3.01 (3 H, s), 6.7–7.5 (3 H, m), 7.58 (1 H, s), 7.73 (1 H, s), 7.83 (1 H, s).
MASS (m/e):353, 275

EXAMPLE 23

The following compound was obtained according to a similar manner to that of Example 22.

4'-Acetyl-2'-(2,4-dichlorophenylthio)methanesulfonanilide mp:190° to 193° C.
IR (Nujol):3250, 1675, 1590 cm$^{-1}$
NMR (DMSO-d$_6$, δ):2.50 (3 H, s), 3.11 (3 H, s), 6.77 (1 H, d, J=8 Hz), 7.2–8.1 (5 H, m), 9.48 (1 H, s)
MASS (m/e):389 (M+), 275

EXAMPLE 24

Sodium borohydride (0.22 g) was added portionwise to a solution of 4'-acetyl-2'-(2,4-dichlorophenylthio)methanesulfonanilide (1.5 g) in tetrahydrofuran (20 ml) and methanol (10 ml) at room temperature. The mixture was stirred for 9 hours, treated with acetic acid, and concentrated under reduced pressure. The residue was dissolved in ethyl acetate, washed with an aqueous solution of sodium bicarbonate, and dried. The solution was evaporated to dryness and the residue was recrystallized from a mixture of ethanol and water to give colorless needles of 2'-(2,4-dichlorophenylthio)-4'-(1-hydroxyethyl)methanesulfonanilide (1.3 g).

mp:91° to 94° C.
IR (Nujol):3380, 3250, 1605, 1550, 1490 cm$^{-1}$
NMR (CDCl$_3$, δ):1.47 (3 H, d, J=8 Hz), 1.95 (1 H, d, J=4 Hz), 2.89 (3 H, s), 4.7–5.0 (1 H, m), 6.55 (1 H, d, J=8 Hz), 6.9–7.8 (6 H, m)
MASS (m/e):391 (M+), 373

EXAMPLE 25

The following compound was obtained according to a similar manner to that of Example 24.

2'-(2,4-Difluorophenylsulfonyl)-4'-(1-hydroxyethyl)-methanesulfonanilide mp:116° to 117° C.
IR (Nujol):3520, 3270, 1605, 1500 cm$^{-1}$
NMR (DMSO-d$_6$, δ):1.32 (3 H, d, J=7 Hz), 3.10 (3 H, s), 4.78 (1 H, q, J=7 Hz), 5.35 (1 H, broad s), 7.2–8.3 (6 H, m), 8.87 (1 H, s)
MASS (m/e):391 (M+), 376

EXAMPLE 26

A mixture of 4'-amino-3'-[N-methyl-N-(2,4-difluorophenyl)aminoacetophenone (1.2 g) and methanesulfonyl chloride (0.6 g) in pyridine was stirred at room temperature for 7 hours. The mixture was evaporated and the residue was stirred with 5% sodium hydroxide (30 ml) overnight. The mixture was washed with toluene, and the aqueous layer was acidified with hydrochloric acid and extracted with ethyl acetate. The extract was concentrated and the residue was recrystallized from ethanol to give pale brown prisms of 4'-acetyl2'-[N-methyl-N-(2,4-difluorophenyl)amino]methanesulfonanilide (0.49 g).

mp:152° to 154° C.
IR (Nujol):3270, 1680, 1600, 1505 cm$^{-1}$
NMR (CDCl$_3$, δ):2.51 (3 H, s), 3.03 (3 H, s), 3.06 (3 H, s), 6.6–7.2 (3 H, m), 7.6–7.9 (4 H, m)
MASS (m/e):354 (M+), 275

EXAMPLE 27

The following compound was prepared according to a similar manner to that of Example 26.

4'-Acetyl-2'-(2,4-dichlorophenylamino)methanesulfonanilide mp:103° to 104° C.
IR (Nujol):3400, 3140, 1670, 1605, 1575, 1490 cm$^{-1}$
NMR (CDCl$_3$, δ):2.53 (3 H, s), 3.07 (3 H, s), 5.97 (1 H, s), 6.45 (1 H, d, J=8 Hz), 7.0–8.0 (6 H, m)
MASS (m/e):372 (M+), 293, 258

EXAMPLE 28

A mixture of 4'-acetyl-2'-aminomethanesulfonanilide (1.6 g) and 2,4-difluorobenzoyl chloride (1.5 g) in pyridine (15 ml) was stirred at 0° C. for 3 hours. The mixture was evaporated and the residue was stirred with 5% sodium hydroxide (40 ml) for 1 hour at room temperature. The mixture was washed with toluene, and the aqueous layer was acidified with hydrochloric acid. The precipitates obtained were recrystallized from a mixture of acetone and ethyl acetate (1:1) to give pale brown needles of N-(5-acetyl-2-methanesulfonamidophenyl)-2,4-difluorobenzamide (1.3 g).

mp:203° to 204° C.
IR (Nujol):3440, 3240, 1690, 1615, 1585, 1535 cm$^{-1}$
NMR (DMSO-d$_6$, δ):2.55 (3 H, s), 3.05 (3 H, s), 7.1–8.1 (5 H, m), 8.30 (1 H, d, J=2 Hz), 9.45 (1 H, s), 9.77 and 9.80 (1 H, s)
MASS (m/e):368 (M+)

EXAMPLE 29

The following compound was obtained according to a similar manner to that of Example 22.

4'-Acetyl-2'-(4-chlorophenylthio)methanesulfonanilide mp:120° to 121° C.
IR (Nujol):3250, 1680, 1595, 1560, 1490 cm$^{-1}$
NMR (CDCl$_3$, δ):2.60 (3 H, s), 2.93 (3 H, s), 7.0–8.3 (8 H, m)
MASS (m/e):355 (M+), 241

EXAMPLE 30

The following compound was prepared according to a similar manner to that of Example 22.

4'-Acetyl-2'-[2-(trifluoromethyl)phenylthio]methanesulfonanilide mp:155° to 157° C.
IR (Nujol):3280, 1680, 1590, 1560 cm$^{-1}$
NMR (DMSO-d$_6$, δ):2.50 (3 H, s), 3.15 (3 H, s), 7.0–8.2 (7 H, m), 9.45 (1 H, s)
MASS (m/e):389 (M+), 310

EXAMPLE 31

The following compound was obtained according to a similar manner to that of Example 22.

4'-Acetyl-2'-(2-chlorophenylthio)methanesulfonanilide mp:139° to 142° C.
IR (Nujol):3280, 1675, 1590, 1560 cm$^{-1}$
NMR (DMSO-d$_6$, δ):2.53 (3 H, s), 3.16 (3 H, s), 6.7–8.2 (7 H, m), 9.52 (1 H, s)
MASS (m/e):355 (M+), 241

EXAMPLE 32

The following compound was obtained according to a similar manner to that of Example 22.

4'-Acetyl-2'-(2-methoxyphenylthio)methanesulfonanilide mp:107° to 109° C.
IR (Nujol):3260, 1670, 1590, 1560 cm$^{-1}$
NMR (DMSO-d$_6$, δ):2.45 (3 H, s), 3.06 (3 H, s), 3.79 (3 H, s), 6.7–8.0 (7 H, m), 9.17 (1 H, s)
MASS (m/e):351 (M+), 214

EXAMPLE 33

The following compound was obtained according to a similar manner to that of Example 13.

2'-(2,4-Difluorophenylthio)-4'-propionylmethanesulfonanilide mp:95° to 97° C.
IR (Nujol):3310, 3240, 1685, 1595, 1490 cm$^{-1}$
NMR (DMSO-d$_6$, δ):1.03 (3 H, t, J=7 Hz), 2.97 (2 H, q, J=7 Hz), 3.18 (3 H, s), 7.0–8.1 (6 H, m), 9.62 (1 H, s)
MASS (m/e):371 (M+)

EXAMPLE 34

The following compound was obtained according to a similar manner to that of Example 22.

4'-Acetyl-2'-(pentafluorophenylthio)methanesulfonanilide mp:122° to 123° C.
IR (Nujol):3280, 1685, 1640, 1590, 1510, 1495 cm$^{-1}$
NMR (DMSO-d$_6$, δ):2.53 (3 H, s), 3.20 (3 H, s), 7.5–8.1 (3 H, m), 9.80 (1 H, broad s)
MASS (m/e):411 (M+), 396

EXAMPLE 35

A mixture of N-ethyl-4-amino-3-(2,4-difluorophenylthio)benzamide (0.84 g) and methanesulfonyl chloride (0.57 g) in pyridine (5 ml) was stirred at room temperature overnight. The reaction mixture was concentrated. The residue was dissolved in ethyl acetate, washed with dilute hydrochloric acid, dried and evaporated. The residue obtained was dissolved in methanol and treated with potassium hydroxide (0.4 g). The solution was concentrated and the residue was dissolved in water. The aqueous solution was acidified with dilute hydrochloric acid and extracted with chloroform. The extract was washed with water, dried, and evaporated. The residual solid was recrystallized from ethanol to give N-ethyl-3-(2,4-difluorophenylthio)-4-(methanesulfonamido)benzamide (0.67 g).

mp:174° to 176° C.
IR (Nujol):3300, 1630, 1600, 1545, 1485 cm$^{-1}$
NMR (CDCl$_3$, δ):1.25 (3 H, t, J=7 Hz), 3.0 (3 H, s), 3.2–3.8 (2 H, m), 6.1–6.4 (1 H, m), 6.7–8.1 (7 H, m)
MASS (m/e):386 (M+), 342

EXAMPLE 36

The following compound was obtained according to a similar manner to that of Example 35.

N-Isopropyl-3-(2,4-difluorophenylthio)-4-(methanesulfonamido)benzamide mp:200° to 201° C.
IR (Nujol):3280, 1630, 1600, 1540, 1485 cm$^{-1}$
NMR (DMSO-d$_6$, δ):1.13 (6 H, d, J=6 Hz), 3.13 (3 H, s), 3.7–4.3 (1 H, m), 7.0–8.4 (7 H, m), 9.47 (1 H, s)
MASS (m/e):400 (M+)

EXAMPLE 37

The following compound was obtained according to a similar manner to that of Example 35.

N-Phenyl-3-(2,4-difluorophenylthio)-4-(methanesulfonamido)benzamide.

mp:187° to 188° C.
IR (Nujol):3325, 3275, 1650, 1600, 1530, 1480 cm$^{-1}$
NMR (DMSO-d$_6$, δ):3.17 (3 H, s), 7.0–8.1 (11 H, m), 9.57 (1 H, s), 10.27 (1 H, s)
MASS (m/e):434 (M+)

EXAMPLE 38

The following compound was obtained according to a similar manner to that of Example 35.

N-Benzyl-3-(2,4-difluorophenylthio)-4-(methanesulfonamido)benzamide mp:166° to 168° C.
IR (Nujol):3360, 3300, 1630, 1600, 1550, 1485 cm$^{-1}$
NMR (DMSO-d$_6$, δ):3.13 (3 H, s), 4.43 (2 H, d, J=6 Hz), 7.0–8.0 (11 H, m), 9.03 (1 H, t, J=6 Hz), 9.50 (1 H, s)
MASS (m/e):448 (M+)

EXAMPLE 39

The following compound was obtained according to a similar manner to that of Example 35.

N,N-Dimethyl-3-(2,4-difluorophenylthio)-4-(methanesulfonamido)benzamide mp:145° to 146° C.
IR (Nujol):3240, 1630, 1600 cm$^{-1}$
NMR (CDCl$_3$δ) 3.00 (3 H, s), 3.04 (6 H, s), 6.7–7.8 (7 H, m)
MASS (m/e):386 (M+), 342

EXAMPLE 40

A mixture of 4'-cyano-2'-(2,4-difluorophenylthio)methanesulfonanilide (4.8 g) and Raney's Nickel (4.8 g) in 75% formic acid (130 ml) was stirred and refluxed for 2 hours. The mixture was filtered and the filtrate was concentrated to dryness. The residue was dissolved in chloroform, washed with an aqueous solution of sodium bicarbonate, dried and evaporated. The oily residue (5 g) was purified by column chromatography on silica gel (100 g) eluting with a mixture of toluene and ethyl acetate (5:1) to give crystals of 2'-(2,4-difluorophenylthio)-4'-formylmethanesulfonanilide (3.0 g).

mp:109° to 111° C.
IR (Nujol):3250, 1700, 1600, 1565, 1485 cm$^{-1}$
NMR (CDCl$_3$, δ):3.08 (3 H, s), 6.7–8.2 (7 H, m), 9.94 (1 H, s)
MASS (m/e):342

EXAMPLE 41

Sodium borohydride (0.11 g) was added portionwise to a solution of 2'-(2,4-difluorophenylthio)-4'-formylmethanesulfonanilide (1 g) in methanol (10 ml) at 10° C. The mixture was stirred at room temperature for 2 hours and evaporated. The residue was dissolved in ethyl acetate, washed with dilute hydrochloric acid and water successively, dried, and concentrated to dryness. The residue was recrystallized from ethanol to give colorless crystals of 2'-(2,4-difluorophenylthio)-4'-(hydroxymethyl)methanesulfonanilide (0.74 g).

mp:78° to 79° C.
IR (Nujol):3250, 1600, 1485 cm$^{-1}$
NMR (CDCl$_3$, δ):1.82 (1 H, broad s), 2.97 (3 H, s), 4.69 (2 H, s), 6.7–7.9 (7 H, m)

EXAMPLE 42

A mixture of 2'-(2,4-difluorophenylthio)-4'-formylmethanesulfonanilide (1 g) and triphenylphosphoranylideneacetone (1.4 g) in dimethylsulfoxide (5 ml) was stirred for 10 hours at 80° C. The mixture was poured into water (50 ml) and extracted with ethyl acetate. The extract was washed with water, dried and evaporated. The oily residue (2.5 g) was purified by column chromatography on silica gel (100 g) eluting with a mixture of toluene and ethyl acetate (1:1) to give crystals (1 g). The crystals were recrystallized from ethanol to give colorless needles of 2'-(2,4-difluorophenylthio)-4'-(3-oxo-1-butenyl)methanesulfonanilide (0.85 g).

mp:119° to 120° C.
IR (Nujol):3280, 1665, 1600, 1500 cm$^{-1}$
NMR (CDCl$_3$, δ):2.37 (3 H, s), 3.00 (3 H, s), 6.5–7.9 (9 H, m)
MASS (m/e):383 (M$^+$)

EXAMPLE 43

A mixture of 4'-(2-amino-4-thiazolyl)-2'-(2,4-difluorophenylthio)methanesulfonanilide hydrobromide (1.2 g) and methanesulfonyl chloride (0.556 g) in pyridine (5 ml) was stirred at room temperature overnight. The reaction mixture was concentrated. The residue was dissolved in ethyl acetate, washed with dilute hydrochloric acid, dried and evaporated. The residue obtained was dissolved in methanol and treated with potassium hydroxide (0.4 g). The solution was concentrated and the residue was dissolved in water. The aqueous solution was acidified with dilute hydrochloric acid and extracted with chloroform. The extract was evaporated to dryness. The residue (1 g) was purified by column chromatography on silica gel (20 g) eluting with a mixture of toluene and ethyl acetate (1:1) followed by recrystallization from ethanol to give crystals of 2'-(2,4-difluorophenylthio)-4'-[2-(methanesulfonamido)-4-thiazolyl]methanesulfonanilide (0.26 g).

mp:159° to 161° C.
IR (Nujol):3550, 3250, 1600, 1535, 1490 cm$^{-1}$
NMR (DMSO-d$_6$, δ):3.00 (3 H, s), 3.13 (3 H, s), 7.1–7.9 (8 H, m), 9.50 (1 H, broad s)
MASS (m/e):490, 412

EXAMPLE 44

A mixture of 4'-bromoacetyl-2'-(2,4-difluorophenylthio)methanesulfonanilide (2.4 g) and 2-aminopyrimidine (0.8 g) in ethanol (30 ml) was refluxed for 4 hours. The mixture was evaporated, and the residue was treated with an aqueous solution of sodium bicarbonate and extracted with ethyl acetate. The extract was evaporated to dryness. The residue was purified by column chromatography on silica gel (20 g) eluting with a mixture of chloroform and methanol (50:1) to give a powder (0.78 g). The powder was recrystallized from a mixture of tetrahydrofuran and ethyl acetate to give crystals of 2'-(2,4-difluorophenylthio)-4'-(imidazo[1,2-a]pyrimidin-2-yl)methanesulfonanilide (0.6 g).

mp:219° to 220° C.
IR (Nujol):3300, 1620, 1590, 1525, 1500 cm$^{-1}$
NMR (DMSO-d$_6$, δ):3.13 (3 H, s), 6.9–8.1 (7 H, m), 8 30 (1 H, s), 8.4–9.1 (2 H, m), 9.47 (1 H, s)
MASS (m/e):432 (M$^+$)

EXAMPLE 45

The following compound was obtained according to a similar manner to that of Example 35 using chloromethanesulfonyl chloride.

4'-Acetyl-2'-(2,4-difluorophenylthio)-1-chloromethanesulfonanilide
mp:74° to 76° C.
IR (Nujol):3250, 1690, 1590, 1560, 1480 cm$^{-1}$
NMR (CDCl$_3$, δ):2.60 (3 H, s), 4.63 (2 H, s), 6.7–8.3 (7 H, m)
MASS (m/e):390, 290

EXAMPLE 46

The following compound was obtained according to a similar manner to that of Example 35 using trifluoromethanesulfonic anhydride.

4'-Acetyl-2'-(2,4-difluorophenylthio)-1,1,1-trifluoromethanesulfonanilide
mp:97° to 100° C.
IR (Nujol):3250, 1680, 1600, 1485 cm$^{-1}$
NMR (CDCl$_3$, δ):2.58 (3 H, s), 6.8–8.2 (7 H, m)
MASS (m/e):411 (M$^+$)

EXAMPLE 47

The following compound was obtained according to a similar manner to that of Example 41.

2'-(2,4-Difluorophenylthio)-4'-(1-hydroxyethyl)-1,1,1-trifluoromethanesulfonanilide
mp:104° to 105° C.
IR (Nujol):3530, 1600, 1485, 1460 cm$^{-1}$
NMR (CDCl$_3$, δ):1.47 (3 H, d, J=7 Hz), 4.88 (1 H, q, J=7 Hz), 6.7–7.8 (6 H, m)

EXAMPLE 48

A mixture of 5-acetyl-2-(methanesulfonamido)benzoic acid (1.5 g) in thionyl chloride (15 ml) was refluxed for 40 minutes. Thionyl chloride was evaporated and coevaporated with toluene to give a solid residue (1.9 g).

A solution of the above solid residue in tetrahydrofuran (10 ml) was added dropwise to an icecooled solution of 2,4-difluoroaniline (2.3 g) in water (5 ml). The mixture was stirred at room temperature for 3 hours and extracted with ethyl acetate. The extract was washed with 3N hydrochloric acid and water successively, dried and concentrated to dryness. The residue (2.6 g) was purified by column chromatography on silica gel (80 g) eluting with a mixture of toluene and ethyl acetate (4:1). The fractions containing the desired compound were combined and concentrated. The residue was recrystallized from ethanol (5 ml) to give N-(2,4-difluorophenyl)-5-acetyl-2-(methanesulfonamido)benzamide (0.97 g).

mp:153° to 155° C.
IR (Nujol):3350, 1670, 1650, 1610, 1600, 1540, 1505 cm$^{-1}$
NMR (DMSO-d$_6$, δ):2.62 (3 H, s), 3.23 (3 H, s), 6.9-7.7 (4 H, m), 8.10 (1 H, dd, J=8.5, 2 Hz), 8.48 (1 H, d, J=2 Hz), 10.60 (1 H, s), 10.85 (1 H, s)
MASS (m/e):368 (M+)

EXAMPLE 49

A mixture of 4'-acetyl-2'-(2,4-difluorophenylamino)methanesulfonanilide (1.5 g), methoxylamine hydrochloride (0.4 g) and pyridine (0.43 ml) in ethanol (15 ml) was refluxed for 3 hours. The mixture was cooled to room temperature. Precipitates were filtered, washed with water, and recrystallized from ethanol to give colorless needles of 2'-(2,4-difluorophenylamino)-4'-[1-(methoxyimino)ethyl]methanesulfonanilide (1.4 g).

mp:150° to 152° C.
IR (Nujol):3410, 3260, 1615, 1575, 1535, 1510 cm$^{-1}$
NMR (CDCl$_3$, δ):2.13 (3 H, s), 3.02 (3 H, s), 3.95 (3 H, s), 5.90 (1 H, s), 6.6-7.5 (7 H, m)
MASS (m/e):369 (M+), 290

EXAMPLE 50

A mixture of 4'-acetyl-2'-(2,4-difluorophenylthio)methanesulfonanilide (2.5 g), ammonium acetate (5.4 g) and sodium cyanoborohydride (0.96 g) in methanol (50 ml) was refluxed for 5 hours. The mixture was concentrated to dryness. The residue was dissolved in ethyl acetate, washed with water, dried, and evaporated. The residue (2.6 g) was purified by column chromatography on silica gel (70 g) eluting with a mixture of chloroform and methanol (9:1) to give a white powder of 4'-(1-aminoethyl)-2'-(2,4-difluorophenylthio)methanesulfonanilide (0.84 g).

mp:165° to 166° C.
IR (Nujol):3120, 1595, 1485 cm$^{-1}$
NMR (DMSO-d$_6$, δ):1.23 (3 H, d, J=7 Hz), 2.73 (3 H, s), 3.98 (1 H, q, J=7 Hz), 5.88 (3 H, broad s), 6.78 (1 H, s), 6.9-7.5 (5 H, m)
MASS (m/e):358 (M+), 343

EXAMPLE 51

A mixture of 4-amino-2-chloro-5-(2,4-difluorophenylthio)benzonitrile (1.5 g), methanesulfonyl chloride (1.9 ml) and triethylamine (2.8 ml) in pyridine (14 ml) was stirred at 5° C. for 3 hours. The mixture was concentrated and the residue was dissolved in ethyl acetate, washed with water, dried, and evaporated to dryness.

The resulting residue (2.8 g) was treated with 4N sodium hydroxide (3.7 ml) in tetrahydrofuran (28 ml) at room temperature for 1 hour. Ethyl acetate and water were added and the mixture was separated. The aqueous layer was acidified with hydrochloric acid and extracted with ethyl acetate. The extract was washed with water, dried and evaporated. The residue was recrystallized from a mixture of ethanol and ethyl acetate to give pale brown crystals of 5'-chloro-4'-cyano-2'-(2,4-difluorophenylthio)methanesulfonanilide (0.9 g).

mp:159° to 162° C.
IR (Nujol):3250, 2240, 1600, 1545, 1485 cm$^{-1}$
NMR (DMSO-d$_6$, δ):3.27 (3 H, s), 7.1-7.7 (3 H, m), 7.76 (2 H, s)
MASS (m/e):374 (M+), 295, 260

EXAMPLE 52

The following compound was obtained according to a similar manner to that of Example 41.

2'-(2,4-Difluorophenylthio)-4'-(1-hydroxypropyl)methanesulfonanilide; an oil.
IR (Film):3500, 3300, 1600, 1480 cm$^{-1}$
NMR (CDCl$_3$, δ):0.93 (3 H, t, J=7 Hz), 1.5-2.1 (3 H, m), 2.98 (3 H, s), 4.4-4.8 (1 H, m), 6.7-7.9 (7 H, m)
MASS (m/e):373 (M+), 343

EXAMPLE 53

Benzyl chloride (1.92 ml) was added dropwise to a mixture of magnesium (357 mg) in tetrahydrofuran (15 ml) at 40° C. The mixture was stirred at room temperature for 40 minutes. To the resulting solution was added a solution of 4'-cyano-2'-(2,4-difluorophenylthio)methanesulfonanilide (1 g) in tetrahydrofuran (15 ml) dropwise at room temperature. The reaction mixture was stirred for 1 hour and hydrolyzed with cold ammonium chloride solution. Ethyl acetate (30 ml) and water (30 ml) were added. The organic layer was separated, shaken with diluted hydrochloric acid, dried, and evaporated. The residual oil (2.2 g) was purified by column chromatography on silica gel (40 g) eluting with a mixture of toluene and ethyl acetate (40:1) followed by recrystallization from ethanol to give pale brown crystals of 2'-(2,4-difluorophenylthio)-4'-(phenylacetyl)methanesulfonanilide (0.52 g).

mp:120° to 122° C.
IR (Nujol):3300, 1680, 1595, 1560, 1485 cm$^{-1}$
NMR (CDCl$_3$, δ):2.97 (3 H, s), 4.15 (2 H, s), 6.7-8.2 (12 H, m)
MASS (m/e):433 (M+)

EXAMPLE 54

The following compound was prepared according to a similar manner to that of Example 22.

4'-Acetyl-2'-(2-pyridylthio)methanesulfonanilide
mp:115° to 116° C.
IR (Nujol):3240, 1680, 1600, 1580 cm$^{-1}$
NMR (CDCl$_3$, δ):2.54 (3 H, s), 3.00 (3 H, s), 7.0-8.4 (7 H, m), 8.87 (1 H, broad s)
MASS (m/e):322 (M+)

EXAMPLE 55

The following compound was obtained according to a similar manner to that of Example 22.

4'-Acetyl-2'-(2-thiazolylthio)methanesulfonanilide
mp:126° to 128° C.
IR (Nujol):3260, 1680, 1600, 1560 cm$^{-1}$
NMR (DMSO-d$_6$, δ):2.57 (3 H, s), 3.15 (3 H, s), 7.6-8.2 (5 H, m), 9.77 (1 H, broad s)
MASS (m/e):328 (M+), 249

EXAMPLE 56

The following compound was prepared according to a similar manner to that of Example 22.

4'-Acetyl-2'-(2-thienylthio)methanesulfonanilide
mp:98° to 99° C.
IR (Nujol):3300, 1675, 1590, 1490 cm$^{-1}$
NMR (DMSO-d$_6$, δ):2.47 (3 H, s), 3.17 (3 H, s), 7.1-8.0 (6 H, m), 9.66 (1 H, broad s)
MASS (m/e):327 (M+)

EXAMPLE 57

The following compound was obtained according to a similar manner to that of Example 22.

4'-Acetyl-2'-(2-quinolylthio)methanesulfonanilide
mp:158° to 159° C.
IR (Nujol):3250, 1675, 1595, 1560, 1495 cm$^{-1}$
NMR (CDCl$_3$, δ):2.60 (3 H, s), 3.02 (3 H, s), 7.2–8.3 (9 H, m), 9.14 (1 H, s)

EXAMPLE 58

The following compound was obtained according to a similar manner to that of Example 22.

4'-Acetyl-2'-(5-methylbenzimidazolyl-2-thio)methanesulfonanilide
mp:187° to 189° C.
IR (Nujol):3300, 1685, 1595, 1490 cm$^{-1}$
NMR (DMSO-d$_6$, δ):2.39 (3 H, s), 2.52 (3 H, s), 3.13 (3 H, s), 6.9–8.1 (6 H, m), 8.07 (1 H, s), 11.3 (1 H, broad s)
MASS (m/e):375 (M+), 296

EXAMPLE 59

The following compound was obtained according to a similar manner to that of Example 51.

4'-Cyano-2'-(thiophene-2-thio)methanesulfonanilide
mp:146° to 147° C.
IR (Nujol):3250, 2220, 1595, 1480 cm$^{-1}$
NMR (DMSO-d$_6$, δ):3.18 (3 H. s), 7.1–8.0 (6 H, m), 9.8 (1 H, broad s)
MASS (m/e):310 (M+), 231

EXAMPLE 60

A solution of bromine (0.156 ml) in acetic acid (2.1 ml) was added dropwise to an ice-cooled solution of 4'-cyano-2'-(thiophene-2-thio)methanesulfonanilide (0.94 g) in dichloromethane (19 ml) and acetic acid (19 ml). The mixture was stirred at 0° C. for 2 hours and concentrated to dryness. The residue was recrystallized from ethanol to give pale yellow crystals of 2'-(5-bromothiophene-2-thio)-4'-cyanomethanesulfonanilide (0.95 g).

mp:115° to 116° C.
IR (Nujol):3250, 2220, 1595, 1480 cm$^{-1}$
NMR (DMSO-d$_6$, δ):3.13 (3 H, s), 7.2–7.8 (5 H, m), 9.8 (1 H, broad s)
MASS (m/e):389 (M+)

EXAMPLE 61

A mixture of 2-amino-5-nitro-2',4'-difluorobenzophenone (5.1 g) and methanesulfonyl chloride (14 ml) in pyridine (40 ml) was stirred at room temperature overnight. The mixture was poured into cold 3N hydrochloric acid (200 ml). The insoluble was filtered and dissolved in a mixture of pyridine (20 ml), ethanol (5 ml) and 5% sodium hydroxide (50 ml). The solution was stirred overnight and washed with toluene. The aqueous layer was acidified with hydrochloric acid and the precipitates were filtered to give brown crystals of 2'-(2,4-difluorobenzoyl)-4'-nitromethanesulfonanilide (5.7 g).

mp:172° to 178° C.
IR (Nujol):3100, 1650, 1615, 1590, 1525, 1490 cm$^{-1}$
NMR (DMSO-d$_6$, δ):3.19 (3 H, s), 7.1–8.5 (7 H, m)

EXAMPLE 62

Sodium borohydride (1.49 g) was added portionwise to a stirred mixture of 2'-(2,4-difluorobenzoyl)-4'-nitromethanesulfonanilide (5.6 g) in tetrahydrofuran (50 ml). The mixture was stirred at room temperature for 4 hours, treated with acetic acid (5 ml) and water (20 ml), had concentrated to dryness. The residue was dissolved in ethyl acetate and washed with water. The organic layer was dried and evaporated to give a powder of 2'-(2,4-difluoro-α-hydroxybenzyl)-4'-nitromethanesulfonanilide (5.3 g).

IR (Film):3500, 3250, 1615, 1590, 1520, 1495 cm$^{-1}$
NMR (DMSO-d$_6$, δ):3.05 (3 H, s), 6.47 (1 H, s), 7.0–8.4 (8 H, m)

EXAMPLE 63

A mixture of 2'-(2,4-difluoro-α-hydroxybenzyl)-4'-nitromethanesulfonanilide (5.3 g), 10% palladium on carbon (1 g) and acetic acid (6 ml) in methanol (60 ml) was shaken under hydrogen atmosphere for 9 hours. The mixture was filtered and the filtrate was evaporated. The residue was dissolved in ethyl acetate, washed with a saturated solution of sodium bicarbonate, dried, and evaporated. The sirupy residue was recrystallized from ethanol to give crystals of 4'-amino-2'-(2,4-difluorobenzyl)methanesulfonanilide (3.2 g).

mp:170° to 172° C.
IR (Nujol):3400, 3330, 1620, 1600, 1500 cm$^{-1}$
NMR (DMSO-d$_6$, δ):2.80 (3 H, s), 5.1 (2 H, s), 5.58 (1 H, d, J=4.5 Hz), 6.18 (1 H, d, J=4.5 Hz), 6.3–7.5 (6 H, m), 8.30 (1 H, s)
MASS (m/e):312 (M+)

EXAMPLE 64

A solution of sodium nitrite (0.79 g) in water (5 ml) was added dropwise to a mixture of 4'-amino-2'-(2,4-difluorobenzyl)methanesulfonanilide (3.0 g) and hydrochloric acid (1.7 ml) in water (15 ml) at 0° to 5° C., and the solution was stirred for 20 minutes at the same temperature. The resulting solution was added dropwise to a mixture of sodium cyanide (1.7 g) and cupric sulfate pentahydrate (3.1 g) in water (25 ml) at 5 to 10° C. N,N-Dimethylformamide (30 ml) was added and the mixture was adjusted to pH 7 with sodium bicarbonate. The mixture was stirred at room temperature for 1 hour and at 60° C. for 4 hours. The reaction mixture was poured into ice-water (200 ml) and extracted with ethyl acetate. The organic layer was washed with water, dried and evaporated. The residue (2.6 g) was purified by column chromatography on silica gel (80 g) eluting with a mixture of toluene and ethyl acetate (5:1) followed by recrystallization from ethanol to give prisms of 4'-cyano-2'-(2,4-difluoro-α-hydroxybenzyl)methanesulfonanilide (1.1 g).

mp:133° to 135° C.
IR (Nujol):3430, 3250, 2240, 1610, 1505 cm$^{-1}$
NMR (DMSO-d$_6$, δ):2.96 (3 H, s), 6.30 (1 H, s), 6.4–7.9 (7 H, m), 9.4 (1 H, broad s)
MASS (m/e):338 (M+), 259, 241

EXAMPLE 65

A mixture of 4'-amino-3'-(2,4-difluorophenylamino)acetophenone (1.6 g), trifluoromethanesulfonic anhydride (2.1 g) and triethylamine (0.75 g) in dichloromethane (15 ml) was stirred overnight at room temperature. The reaction mixture was concentrated. The residue was dissolved in ethanol (5 ml) and treated with 5% sodium hydroxide solution (30 ml). Water (30 ml) was added and the resulting solution was washed with toluene. The aqueous layer was acidified with hydrochloric acid and extracted with ethyl acetate. The extract was washed with water, dried and evaporated.

The residue (1.9 g) was purified by column chromatography on silica gel (60 g) eluting with a mixture of chloroform and methanol (9:1) to give an oil of 4'-acetyl-2'-(2,4-difluorophenylamino)-1,1,1-trifluoromethanesulfonanilide (1.1 g).

IR (Film):3400, 1660, 1590, 1510 cm$^{-1}$
NMR (DMSO-d$_6$, δ):2.43 (3 H, s), 6.0 (2 H, broad s), 6.8–7.6 (6 H, m)
MASS (m/e):394 (M+), 261, 241

EXAMPLE 66

The following compound was prepared according to a similar manner to that of Example 35.

3-(2,4-Difluorophenylamino)-4-(methanesulfonamido)benzamide
mp:197° to 199° C.
IR (Nujol):3400, 3290, 3220, 1650, 1620, 1580, 1535, 1505 cm$^{-1}$
NMR (DMSO-d$_6$, δ):3.03 (3 H, s), 7.0–7.6 (8 H, m), 7.90 (1 H, broad s), 9.18 (1 H, s)
MASS (m/e):341 (M+)

EXAMPLE 67

The following compound was prepared according to a similar manner to that of Example 35.

N-Methyl-3-(2,4-difluorophenylamino)-4-(methanesulfonamido)benzamide
mp:147° to 149° C.
IR (Nujol):3400, 3270, 1615, 1580, 1525, 1505 cm$^{-1}$
NMR (DMSO-d$_6$, δ):2.73 (3 H, d, J=7 Hz), 3.03 (3 H, s), 7.0–7.6 (7 H, m), 8.32 (1 H, q, J=7 Hz), 9.17 (1 H, s)
MASS (m/e):355 (M+), 276

EXAMPLE 68

A mixture of 4'-amino-3'-chloro-5'-(2,4-difluorophenylthio)acetophenone (1 g) and methanesulfonic anhydride (1.2 g) in pyridine (5 ml) was stirred at room temperature for 2 days. The mixture was concentrated. The residue was dissolved in chloroform, washed with dilute hydrochloric acid, dried and evaporated. The residue was dissolved in methanol (30 ml) and treated with potassium hydroxide (0.4 g) for 30 minutes. The solution was concentrated and the residue was dissolved in water and washed with chloroform. The aqueous layer was acidified with hydrochloric acid and extracted with chloroform. The extract was washed with water, dried and evaporated. The residual oil was recrystallized from ethanol to give crystals of 4'-acetyl2'-chloro-6'-(2,4-difluorophenylthio)methanesulfonanilide (0.54 g).
mp:145° to 146° C.
IR (Nujol):3270, 1690, 1600, 1550 cm$^{-1}$
NMR (CDCl$_3$, δ):2.48 (3 H, s), 3.41 (3 H, s), 6.6–8.0 (6 H, m)
MASS (m/e):390, 312

EXAMPLE 69

Methyl nitrite [prepared from sodium nitrite (1.4 g), methanol (0.9 ml) and sulfuric acid (0.7 ml) in water (2.3 ml)] was introduced into an ice-cooled mixture of 2'-(2,4-difluorophenylthio)-4'-propionylmethanesulfonanilide (2.54 g) in tetrahydrofuran (10 ml) and 12% hydrogen chloride in ether (10 ml). The mixture was stirred for 5 hours at 3° C. and evaporated. The residual solid was recrystallized from ethanol to give colorless crystals of 2'-(2,4-difluorophenylthio)-4'[2-(hydroxyimino)-1-oxopropyl]methanesulfonanilide (2.5 g).

mp:140° to 143° C.
IR (Nujol):3360, 3250, 1675, 1600, 1490 cm$^{-1}$
NMR (CDCl$_3$, δ):2.20 (3 H, s), 3.0 (3 H, s), 6.7–8.2 (7 H, m), 8.65 (1 H, s)
MASS (m/e):400 (M+), 341

EXAMPLE 70

A mixture of 2'-(2,4-difluorophenylthio)-4'-[2-(hydroxyimino)-1-oxopropyl]methanesulfonanilide (1.7 g) in hydrochloric acid (8 ml) was refluxed for 2 hours. The mixture was extracted with ethyl acetate. The extract was washed with water and sodium bicarbonate solution successively, dried, and evaporated. The residual oil (1.5 g) was purified by column chromatography on silica gel (30 g) eluting with a mixture of toluene and ethyl acetate (5:1) followed by recrystallization from ethanol to give yellow needles of 2'-(2,4-difluorophenylthio)-4'-pyruvoylmethanesulfonanilide (0.6 g).
mp:108° to 109° C.
IR (Nujol):3300, 1715, 1670, 1590, 1485 cm$^{-1}$
NMR (CDCl$_3$, δ):2.53 (3 H, s), 3.07 (3 H, s), 6.7–8.4 (7 H, m)
MASS (m/e):385 (M+), 342

EXAMPLE 71

The following compound was prepared according to a similar manner to that of Example 41.

2'-(2,4-Difluorophenylthio)-4'-(1-hydroxy-2-phenylethyl)methanesulfonanilide
mp:83° to 84° C.
IR (Nujol):3450, 3270, 1595, 1485 cm$^{-1}$
NMR (DMSO-d$_6$, δ):2.80 (2 H, d, J=6 Hz), 3.03 (3 H, s), 4.5–4.9 (1 H, m), 5.31 (1 H, d, J=5 Hz), 6.9–7.6 (11 H, m), 9.23 (1 H, s)
MASS (m/e):435 (M+), 343

EXAMPLE 72

The following compound was prepared according to a similar manner to that of Example 51.
4'-Acetyl-2'-(phenylthio)methanesulfonanilide
mp:76° to 78° C.
IR (Nujol):3360, 1685, 1595, 1485 cm$^{-1}$
NMR (DMSO-d6, δ):2.52 (3 H, s), 3.13 (3 H, s), 7.40 (5 H, s), 7.5–8.1 (3 H, m), 9.42 (1 H, s)
MASS (m/e):321 (M+ ), 242

EXAMPLE 73

The following compound was obtained according to a similar manner to that of Example 51.
4'-Acetyl-2'-(1-methyltetrazole-5-thio)methanesulfonanilide.
mp:167° to 168° C.
IR (Nujol):3270, 1685, 1595, 1565 cm$^{-1}$
NMR (DMSO-d$_6$, δ):2.51 (3 H, s), 3.09 (3 H, s), 3.98 (3 H, s), 7.61 (1 H, d, J=9 Hz), 7.9–8.1 (2 H, m), 9.7 (1 H, s).

EXAMPLE 74

The following compound was obtained according to a similar manner to that of Example 35.
N-(N,N-Diethylaminoethyl)-3-(2,4-difluorophenylthio)-4(methanesulfonamido)benzamide hydrochloride.
IR (Film):3300, 2625, 2500, 1660, 1645, 1600, 1540, 1485 cm$^{-1}$
NMR (CDCl$_3$-CD$_3$OD, δ):1.32 (6 H, t, J=7 Hz), 3.03 (3 H, s), 3.17 (4 H, q, J=7 Hz), 3.1–3.8 (4 H, m), 6.7–8.0 (6 H, m).

EXAMPLE 75

A mixture of 4'-acetyl-2'-(2-thiazolylthio)methanesulfonanilide (0.74 g), acetic acid (7.4 ml) and hydrogen peroxide (0.67 ml) was stirred at 70° C. for 1.5 hours. The mixture was cooled to 0° C. and the precipitates were filtered, washed with ethyl acetate and dried to give colorless crystals of 4'-acetyl-2'-(2-thiazolylsulfonyl)methanesulfonanilide (0.52 g).

mp:222° to 223° C. (dec.)
IR (Nujol):1690, 1580, 1510 cm$^{-1}$
NMR (DMSO-d$_6$, δ):2.65 (3 H, s), 3.88 (3 H, s), 7.1-8.6 (6 H, m)
MASS (m/e):360 (M$^+$)

We claim:

1. Alkanesulfonanilide derivatives of the formula:

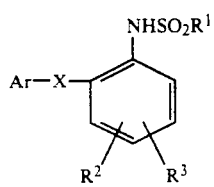

wherein
Ar is a group of the formula:

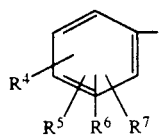

wherein $R^4$ and $R^5$ are each halogen, and $R^6$ and $R^7$ are each hydrogen,
X is —S— or —NH—,
$R^1$ is lower alkyl, $R^2$ is lower alkanoyl and
$R^3$ is hydrogen, or pharmaceutically acceptable salts thereof.

2. A compound according to claim 1, wherein $R^1$ is methyl, $R^2$ is acetyl.

3. A compound according to claim 1, which is 4'-acetyl-2'-(2,4-difluororphenylthio)methanesulfonanilide or 4'-acetyl-2'-(2,4-difluorophenylamino)methanesulfonanilide.

4. An antiinflammatory composition comprising as an effective ingredient an alkanesulfonanilide derivative as defined in claim 1 or pharmaceutically acceptable salt thereof.

5. An analgesic composition comprising as an effective ingredient an alkanesulfonanilide derivative as defined in claim 1 or pharmaceutically acceptable salt thereof.

6. A method for treatment of rheumatic disease which comprises administering to a subject an effective amount of an alkanesulfonanilide derivative as defined in claim 1 or pharmaceutically acceptable salt thereof.

7. A method of treatment of inflammatory disease or pain which comprises administering to a subject an effective amount of an alkanesulfonanilide derivative as defined in claim 1 or pharmaceutically acceptable salt thereof.

8. Alkanesulfonanilide derivatives of the formula

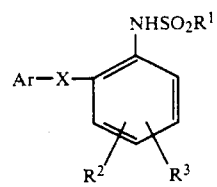

wherein
Ar is a group of the formula:

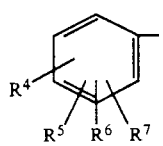

wherein $R^4$ and $R^5$ are each halogen, and $R^6$ and $R^7$ are each hydrogen,
X is —S—,
$R^1$ is lower alkyl,
$R^2$ is carbamoyl or a group of the formula:

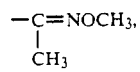

and
$R^3$ is hydrogen, or pharmaceutically acceptable salts thereof.

9. A compound according to claim 8, which is 3-(2,4-difluorophenylthio)-b 4-(methanesulfonamido)-benzamide or 2'-(2,4-difluorophenylthio)-4'-methanesulfonanilide.

10. A compound according to claim 8, which is 3-(2,4-difluorophenylthio)-b 4-(methanesulfonamido) benzamide.

11. An antiinflammatory composition comprising as an effective ingredient an alkanesulfonanilide derivative as defined in claim 8 or pharmaceutically acceptable salt thereof.

12. An analgesic composition comprising as an effective ingredient an alkanesulfonanilide derivative as defined in claim 8 or pharmaceutically acceptable salt thereof.

13. A method for treatment of inflammatory disease or pain which comprises administering to a subject an effective amount of an alkanesulfonanilide derivative as defined in claim 8 or pharmaceutically acceptable salt thereof.

14. A method for treatment of rheumatic disease which comprises administering to a subject an effective amount of alkanesulfonanilide derivative as defined in claim 8 or pharmaceutically acceptable salt thereof.

* * * * *

UNITED STATES PATENT AND TRADEMARK OFFICE
CERTIFICATE OF CORRECTION

PATENT NO. : 5,034,417

DATED : July 23, 1991

INVENTOR(S) : Masaaki MATSUO et al

It is certified that error appears in the above-identified patent and that said Letters Patent is hereby corrected as shown below:

In Column 1, line 50, "COHN" should read -- CONH --.

line 40, "(lower" should read -- (lower) --.

In Column 17, line 14, "Water as" should read -- Water was --.

In Column 19, line 26, "(m/e):234" should read -- (m/e):235 --.

In Column 20, line 8, "(DMSOd$_6$" should read -- (DMSO-d$_6$ --.

line 15, "as" should read -- was --.

line 25, "3 6-4 3" should read -- 3.6-4.3--.

In Column 21, line 26, "'-Amino" should read -- 4'-Amino --.

line 56, "(DMSOd$_6$" should read -- (DMSO-d$_6$ --.

In Column 22, line 41, "(DMSOd$_6$" should read --(DMSO-d$_6$ --.

UNITED STATES PATENT AND TRADEMARK OFFICE
CERTIFICATE OF CORRECTION

PATENT NO. : 5,034,417

DATED : July 23, 1991

INVENTOR(S) : Masaaki MATSUO et al

It is certified that error appears in the above-identified patent and that said Letters Patent is hereby corrected as shown below:

In Column 23, line 13, delete 30.

line 32, "(DMSOd$_6$" should read --(DMSO-d$_6$ --.

line 56, "-4nitrobenz-" should read

-- -4-nitrobenz- --.

In Column 24, line 10, "N-ethyl4" should read -- N-ethyl-4 --.

line 45, "N-phenyl3" should read -- N-phenyl-3 --.

line 69, "(M )" should read -- (M$^+$) --.

In Column 25, line 67, "(DMSOd$_6$" should read -- (DMSO-d$_6$ --.

In Column 26, line 13, "(DMSOd$_6$" should read -- (DMSO-d$_6$ --.

In Column 27, line 5, "Ndiemthylformamide" should read -- N-dimethylformamide --.

UNITED STATES PATENT AND TRADEMARK OFFICE
CERTIFICATE OF CORRECTION

PATENT NO. : 5,034,417

DATED : July 23, 1991

INVENTOR(S) : Masaaki MATSUO et al

It is certified that error appears in the above-identified patent and that said Letters Patent is hereby corrected as shown below:

In Column 28, line 35, ")7.2-8.1" should read -- ): 7.2-8.1 --.

In Column 30, line 31, "(1 1)" should read -- (1 ℓ) --.

In Column 32, line 16, add a period to the end of line.

line 68, "cm " should read -- $cm^{-1}$ --.

In Column 33, line 39, delete second methanesulfonanilide.

In Column 35, line 47, "evporated" should read -- evaporated --.

In Column 36, line 21, "4'-acetyl2'" should read -- 4'-acetyl-2' --.

In Column 37, line 8, delete 35.

In Column 38, line 31-32, "4'-acetyl2'" should read -- 4'-acetyl-2' --.

UNITED STATES PATENT AND TRADEMARK OFFICE
CERTIFICATE OF CORRECTION

PATENT NO. : 5,034,417

DATED : July 23, 1991

INVENTOR(S) : Masaaki MATSUO et al

It is certified that error appears in the above-identified patent and that said Letters Patent is hereby corrected as shown below:

In Column 39, line 5, "'-Acetyl-2'" should read -- 4'-Acetyl-2' --.

In Column 40, line 36, delete period at the end of line.

line 62, "(CDCl$_3$" should read -- (CDCl$_3$, --.

In Column 42, line 23 "8" should read -- 8. --.

In Column 45, line 28, "(3H.s)" should read -- (3H,s) --.

In Column 46, line 2, "had" should read -- and --.

In Column 47, line 51, "acetyl2'" should read -- acetyl-2' --.

In Column 48, line 64, "-4(" should read -- -4-( --.

line 66, add a period at the end of line.

UNITED STATES PATENT AND TRADEMARK OFFICE
CERTIFICATE OF CORRECTION

PATENT NO. : 5,034,417

DATED : July 23, 1991

INVENTOR(S) : Masaaki MATSUO et al

It is certified that error appears in the above-identified patent and that said Letters Patent is hereby corrected as shown below:

In Column 49, line 2, "and hydrogen" should read -- and 30% hydrogen --.

line 60, "method of treatment" should read -- method for treatment --.

In Column 50, line 38, "difluorophenylthio)-b" delete -- -b --.

line 42, "difluorophenylthio)-b" delete -- -b --.

Signed and Sealed this

Fourth Day of May, 1993

Attest:

MICHAEL K. KIRK

Attesting Officer     Acting Commissioner of Patents and Trademarks